(12) United States Patent
Bohach

(10) Patent No.: US 6,541,013 B1
(45) Date of Patent: Apr. 1, 2003

(54) METHODS AND COMPOSITIONS FOR SUPPRESSING BOVINE LEUKEMIA VIRUS WITH A SHIGA TOXIN POLYPEPTIDE

(75) Inventor: Carolyn H. Bohach, Moscow, ID (US)

(73) Assignee: Idaho Research Foundation, Inc., Moscow, ID (US)

( * ) Notice: Subject to any disclaimer, the term of this patent is extended or adjusted under 35 U.S.C. 154(b) by 0 days.

(21) Appl. No.: 09/615,179

(22) Filed: Jul. 13, 2000

(51) Int. Cl.$^7$ ...................... A61K 39/108; A61K 39/02; A61K 38/00; A01N 37/18
(52) U.S. Cl. ............................... 424/241.1; 424/236.1; 514/2
(58) Field of Search .................. 424/236.1, 241.1, 424/520; 514/2

(56) References Cited

U.S. PATENT DOCUMENTS

| | | |
|---|---|---|
| 4,724,205 A | 2/1988 | Karlsson et al. |
| 4,859,769 A | 8/1989 | Karlsson et al. |
| 5,204,097 A | 4/1993 | Arnon et al. |
| 5,220,014 A | 6/1993 | Ackerman et al. |
| 5,378,688 A | 1/1995 | Nett et al. |
| 5,552,144 A | 9/1996 | Samuel et al. |
| 5,552,294 A | 9/1996 | Thorne |
| 5,620,858 A | 4/1997 | Armstrong et al. |
| 5,679,653 A | 10/1997 | Armstrong et al. |
| 5,744,580 A | 4/1998 | Better et al. |
| 5,747,028 A | 5/1998 | Calderwood |
| 5,756,699 A | 5/1998 | Better et al. |
| 5,762,941 A | 6/1998 | Sansonetti et al. |
| 5,795,717 A | 8/1998 | Nakayama et al. |
| 5,801,145 A | 9/1998 | Gariépy |
| 5,807,879 A | 9/1998 | Rosebrough |
| 5,837,491 A | 11/1998 | Better et al. |
| 5,849,714 A | 12/1998 | Rafter et al. |
| 5,888,750 A | 3/1999 | Vanmaele et al. |
| 5,922,848 A | 7/1999 | Vanmaele et al. |
| 5,955,293 A | 9/1999 | Keusch et al. |
| 5,955,449 A | 9/1999 | Armstrong et al. |
| 5,962,423 A | 10/1999 | Bundle et al. |
| 5,965,128 A | 10/1999 | Doyle et al. |
| 5,965,406 A | 10/1999 | Murphy |
| 5,968,894 A | 10/1999 | Lingwood et al. |
| 5,981,568 A | 11/1999 | Kunz et al. |
| 6,013,506 A | 1/2000 | Wardley et al. |
| 6,015,897 A | 1/2000 | Theodore et al. |
| 6,018,022 A | 1/2000 | Read et al. |

OTHER PUBLICATIONS

Menge et al., Infection and Immunity 67/5:2209–2217, May 1999.*
Sandvig et al., The EMBO Journal 19/22:5943–5950, 2000.*
Benigni, F., et al., "Preclinical evaluation of the ribosome–inactivating proteins PAP–1, PAP–S, and RTA in mice," *Int. J. Immunopharmacol.* 17(10):829–839 (1995). (Abstract).

Menge, C., et al., "Shiga toxin 1 from *Escherichia coli* blocks activation and proliferation of bovine lymphocyte subpopulations in vitro," *Infect. Immun.* 67(5):2209–17 (1991).
Sparapani, M., et al., "Toxicity of ricin and volkensin, two ribosome–inactivating proteins, to microglia, astrocyte, and neuron cultures," *Glia* 20(3):203–209 (1997).
Wachinger, M., et al., "Bryodin, a single–chain ribosome–inactivating protein, selectively inhibits the growth of HIV–1–infected cells and reduces HIV–1 production," *Res. Exp. Med.* 193(1):1–12 (1993). (Abstract).
Watanabe, K., et al, "Actions of pokeweed antiviral protein on virus–infected protoplasts," *Biosci. Biotechnol. Biochem.* 61(6):994–997 (1997). (Abstract).
Yoshida, T., et al., "Primary cultures of human endothelial cells are susceptible to low doses of Shiga toxins and undergo apoptosis," *J. Infect. Dis.* 180(6):2048–2052 (1999). (Abstract).
Austin, P.R., and C.J. Hovde, "Purification of Recombinant Shiga–like Toxin Type I B Subunit," *Protein Expression and Purification* 6:771–779 (1995).
Baliga, V., and J.F. Ferrer, "Expression of the Bovine Leukemia Virus and its Internal Antigen in Blood Lymphocytes" *Proc. Soc. Exp. Biol. Med.* 156:388–391 (1977).
Bast, D.J., et al., "Murine Antibody Responses to the Verotoxin 1 B Subunit: Demonstration of Major Histocompatibility Complex Dependence and an Immunodominant Epitope Involving Phenylalanine 30," *Infect. Immun.* 65(7):2978–2982 (1997).
Bruck, C., et al., "Biologically Active Epitopes of Bovine Leukemia Virus Glycoprotein gp51: Their Dependence on Protein Glycosylation and Genetic Variability," *Virology* 136:20–31 (1984).
Driscoll, D.M., et al., "Inhibition of bovine leukemia virus release by antiviral antibodies," *Arch. Virol.* 55(1–2):139–144 (1977).
Gupta, P., et al., "Transcriptional Control of the Bovine Leukemia Virus Genome: Role and Characterization of a Nonimmunoglobulin Plasma Protein From Bovine Leukemia Virus–Infected Cattle," *J. Virol.* 50(1):267–270 (1984).
Hovde, C.J., et al., "Evidence that glutamic acid 167 is an active–site residue of Shiga–like toxin,"*Proc. Natl. Acad. Sci. USA* 85:2568–2572 (1988).

(List continued on next page.)

*Primary Examiner*—James Housel
*Assistant Examiner*—Zachariah Lucas
(74) *Attorney, Agent, or Firm*—Christensen O'Connor Johnson Kindness PLLC

(57) ABSTRACT

The present invention provides methods and compositions for suppressing bovine leukemia-related cell proliferation. In the methods, a Shiga-toxin composition is administered in an amount effective to suppress bovine leukemia-related cell proliferation. The Shiga-toxin composition can include a Shiga-toxin polypeptide; a probiotic microorganism expressing a Shiga-toxin polypeptide; or a transgenic plant expressing a Shiga-toxin polypeptide. In one embodiment, the Shiga-toxin polypeptide is Stx1A and, in another embodiment, the Shiga-toxin polypeptide is Stx1 holotoxin.

9 Claims, 4 Drawing Sheets

OTHER PUBLICATIONS

Jensen, W.A., et al., "In vitro expression of bovine leukemia virus in isolated B–lymphocytes of cattle and sheep," *Vet. Immunol. Immunopathol.* 26:333–342 (1990).

Kidd, L.C., and K. Radke, "Lymphocyte Activators Elicit Bovine Leukemia Virus Expression Differently as Asymptomatic Infection Progresses," *Virology 217:*167–77 (1996).

Mirsky, M.L., et al., "The Prevalence of Proviral Bovine Leukemia Virus in Peripheral Blood Mononuclear Cells at Two Subclinical Stages of Infection," *J. Virol.* 70(4):2178–2183 (1996).

Pirro, F., et al., "Neutralizing antibodies against Shiga–like toxins from *Escherichia coli* in colostra and sera of cattle," *Vet. Microbiol.* 43:131–141 (1995).

Portetelle, D., et al., "In Animals Infected by Bovine Leukemia Virus (BLV) Antibodies to Envelope Glycoprotein gp51 Are Directed Against the Carbohydrate Moiety," *Virology 105*:223–33 (1980).

Stirpe, F., et al., "Ribosome–Inactivating Proteins From Plants: Present Status and Future Prospects," *Bio–Technology 10*:405–412 (1992).

Takashima, I., and C. Olson, "Relation of Bovine Leukosis Virus Production on Cell Growth Cycle," *Arch. Virol.* 69(2):141–148 (1981).

Trueblodd, E.S., et al., "B–Lymphocyte Proliferation During Bovine Leukemia Virus–Induced Persistent Lymphocytosis Is Enhanced by T–Lymphocyte–Derived Interleukin–2," *J. Virol.* 72(4):3169–3177 (1998).

Zandomeni, R.O., et al, "Induction and inhibition of bovine leukemia virus expression in naturally infected cells," *J. Gen. Virol.* 73:1915–1927 (1992).

Zollman, T.M., et al., "Purification of Recombinant Shiga-–Like Toxin Type I $A_1$ Fragment From Escherichia coli," *Protein Expression and Purification* 5:291–295 (1994).

* cited by examiner

METHODS AND COMPOSITIONS FOR SUPPRESSING BOVINE LEUKEMIA VIRUS WITH A SHIGA TOXIN POLYPEPTIDE

This invention was made in part with governmental support under grant AI33981 awarded by the National Institutes of Health and NRICGP grant 95-37201-1979 awarded by the U.S. Department of Agriculture.

FIELD OF THE INVENTION

The present invention relates to methods and compositions for suppressing bovine leukemia virus-related lymphocyte proliferation using a Shiga-toxin polypeptide.

REFERENCES

Full citations for the publications referenced herein are found at the end of the specification immediately preceding the claims. The disclosures of these references and cited patent documents are incorporated herein by reference in their entirety.

ABBREVIATIONS

Abbreviations used are as follows:

| | |
|---|---|
| BLV | bovine leukemia virus |
| PL | persistent lymphocytosis |
| SLP | spontaneous lymphocyte proliferation |
| PBMC | peripheral blood mononuclear cells |
| Stx1 | Shiga-toxin type 1 holotoxin |
| Stx1 A | Shiga-toxin type 1 subunit A |
| Stx1 B | Shiga-toxin type 1 subunit B |

BACKGROUND OF THE INVENTION

Bovine Leukemia Virus (BLV) is an oncogenic retrovirus responsible for the erizootic form of bovine lymphosarcoma, the most frequent malignancy of domestic cattle (Ferrer 1980). BLV infection results in a 1–8 year long asymptomatic period (Ferrer et al. 1979), followed by development of persistent lymphocytosis (PL) in approximately 30% of infected cattle with progression to a malignant lymphosarcoma in fewer than 10% of the animals (Ferrer et al. 1979). The PL stage is a benign neoplasia of B lymphocytes, which are the predominant or exclusive targets of BLV (Esteban et al. 1985). This stage of infection is associated with an increased percentage of peripheral B lymphocytes containing provirus as well as increased viral gene expression (Mirsky et al. 1996). The development of PL markedly enhances the probability of transmission (Mammerickx et al. 1987). The critical importance of PL to transmission of this blood-borne disease was demonstrated by experiments showing that it required significantly less blood from cattle with persistent lymphocytosis to transmit BLV than blood from infected cattle which did not have persistent lymphocytosis (Mammerickx et al. 1987). Moreover, vertical transmission from BLV-infected dams to their calves has been shown to be strongly correlated with persistent lymphocytosis (Agresti et al. 1993).

In cattle, the ability to transmit BLV varies (Weber et al. 1983; Mammerickx et al. 1987), and expression of antigen after in vitro culture has been shown to correlate with infectivity (Miller et al. 1985). The level of BLV expression in the animal also may correlate with the probability of development of persistent lymphocytosis (Cockerell et al. 1988; Dropulic et al. 1992). Moreover, persistent lymphocytosis is a strong risk factor for development of lymphoma. In 1–10% of the animals with persistent lymphocytosis, B cell clones undergo neoplastic transformation, leading to leukemia or lymphoma (Ferrer et al. 1979), and cattle with persistent lymphocytosis are three times more likely to develop lymphoma than infected cattle without persistent lymphocytosis (Ferrer et al. 1979).

BLV is prevalent in dairy operations, with up to 89% of the U.S. dairy operation seropositive for BLV (Howie 1997). Not only does the virus kill cattle, milk and fat yields in BLV-infected cows with persistent lymphocytosis are greatly reduced (Da et al., 1993). Moreover, BLV also produces malignant lymphomas in sheep (Wittman et al. 1989). However, the greatest economic impact of BLV infection in the United States arises from the fact that several countries will not import cattle from BLV-infested areas. Although various attempts have been made to develop a vaccine against BLV infection, an effective vaccine to protect cattle or sheep is not available (Miller et al. 1978; Theilen 1982). BLV infection is thus a costly impediment to cattle production.

Peripheral blood mononuclear cells (PBMC) from BLV-infected cattle proliferate spontaneously in vitro (Takashima & Olson 1981; Thorn et al. 1981). This spontaneous lymphocyte proliferation (SLP) is particularly vigorous in PBMC cultures from cattle in the PL stage of infection. Derepression of viral gene transcription and the synthesis of viral proteins precede SLP (Kettmann et al. 1976; Baliga & Ferrer 1977; Ferrer 1980). Therefore, SLP provides a tractable model system for identifying factors that are capable of preventing BLV-induced neoplasia and malignant lymphoma in infected cattle. The present invention shows that Shiga toxin type 1 (Stx1) is a potent and selective inhibitor of BLV-induced SLP.

Stx1 belongs to a large family of ribosome-inactivating proteins (RIPs) that are found in a variety of higher plants and some bacteria. Class 1 RIPs are N-glycosidases that inactivate ribosomes by removing a single adenine in a specific ribosomal RNA sequence (Endo et al. 1987; Igarishi et al. 1987; Endo et al. 1988). Class 2 RIPs are composed of an A subunit homologous to class 1 RIPs, noncovalently joined to one or more B subunits, usually galactose-specific lectins, that facilitate toxin binding and uptake into target cells. Stx1 is a class 2 RIP composed of an A subunit associated with a pentamer of receptor-binding B subunits. Because of their ability to bind to target cells, class 2 RIPs are potent cytotoxins. Stx1 is toxic to cells that express high levels of the toxin receptor, globotriosylceramide (Gb3 or CD77), most notably Vero cells and human glomerular endothelial cells (Jackson 1990).

Plant RIPs of both class 1 (e.g., pokeweed antiviral protein, titrin, trichosanthin) and class 2 (e.g., ricin) have potent antiviral activities (Stirpe et al. 1992). These compounds often inhibit viral proliferation in mammalian cells in vitro, and some have been tested in vivo in clinical or laboratory settings. For example, ricin can eliminate latent herpes simplex virus in mice (Hino et al. 1988). Other plant RIPs inhibited replication of human immunodeficiency virus type 1 (HIV1) in human peripheral blood mononuclear cells at concentrations nontoxic to uninfected cells (Olson et al. 1991; Lee-Huang et al. 1995).

One problem associated with using RIPs as general antiviral agents is their specificity (Wachinger et al. 1993; Watanabe et al. 1997). For example, the RIP Bryodin selectively inhibits the growth of HIV-1-infected cells, whereas RIPs gelonin and ricin did not (Wachinger et al. 1993). Another concern is that RIPs are highly cytotoxic (Benigni et al. 1995; Sparapani et al. 1997; Yoshida et al. 1999). Therefore, although the antiviral effects of some RIPs are known, the use of RIPs as antiviral agents has not been generally applicable. Surprisingly, it has been discovered that Stx1 strongly inhibits BLV-related cell proliferation and BLV expression. Specifically, this activity is manifested by subunit A of Stx1, which is nontoxic to ruminants or humans.

SUMMARY OF THE INVENTION

The present invention provides methods and compositions for suppressing BLV-related lymphocyte proliferation. The method utilizes a composition that provides a Shiga-toxin polypeptide having antiviral activity.

In one aspect, a method for suppressing BLV-related lymphocyte proliferation is provided. In the method, the proliferation of BLV-infected cells is suppressed by administering an amount of a Shiga-toxin polypeptide having antiviral activity effective to suppress BLV-related lymphocyte proliferation. The administration of the Shiga-toxin polypeptide can prevent or treat the manifestations of BLV infection. In one embodiment, a purified Shiga-toxin polypeptide having antiviral activity is administered. In another embodiment, a naturally occurring microorganism expressing a Shiga-toxin polypeptide having antiviral activity is administered. In a further embodiment, a Shiga-toxin-expressing microorganism that has been modified to eliminate expression of the B subunit of the holotoxin is administered. In yet another embodiment, a microorganism that has been modified to express a Shiga-toxin polypeptide having antiviral activity is administered. In another embodiment, a transgenic plant that has been modified to express a Shiga-toxin polypeptide having antiviral activity is administered.

In another aspect of the invention, compositions for delivering a Shiga-toxin polypeptide are provided. In one embodiment, the invention provides a microorganism genetically modified to express a Shiga-toxin polypeptide having antiviral activity. In another embodiment, a Shiga-toxin-expressing microorganism that has been modified to eliminate expression of the B subunit of the holotoxin is provided. In a further embodiment, a transgenic plant genetically modified to express a Shiga-toxin polypeptide having antiviral activity is provided. In yet another embodiment, a composition is provided that includes a naturally occurring microorganism that expresses a Shiga-toxin polypeptide.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE INVENTION

Figure 1A:
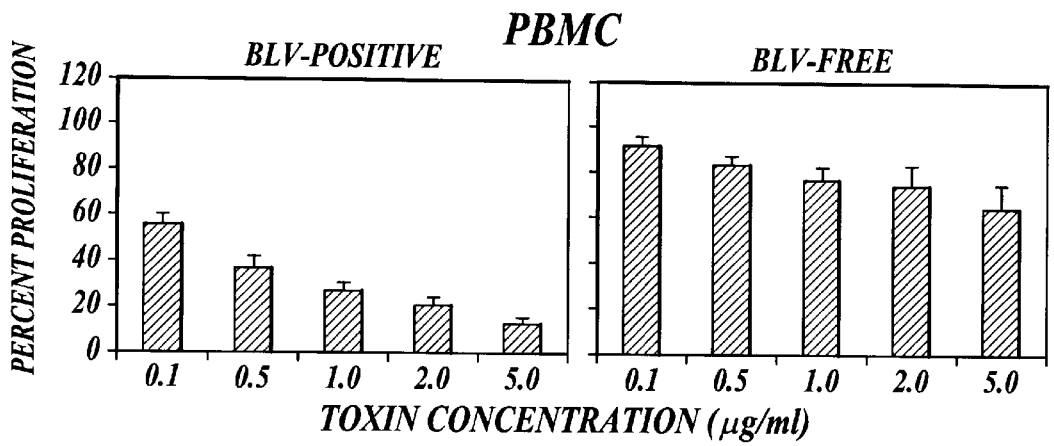
FIGS. 1A–1C illustrate the effect of Stx1 on lymphocyte proliferation. PBMC from persistently lymphocytotic (BLV-positive) or healthy (BLV-negative) cows were incubated with Stx1 holotoxin or subunits (A, A subunit; B, B subunit; and C, holotoxin). BLV-negative cells were induced to proliferate by pokeweed mitogen (5.0 $\mu$g/ml). Cell proliferation was measured as incorporation of tritiated thymidine and expressed as a percentage of the cell proliferation in identical cultures without toxin. Data are means±standard error from three (holotoxin) or ten (Stx1 subunits) experiments. ND refers to not done.

The present invention provides methods and compositions for suppressing BLV-related cell proliferation by administering a Shiga-toxin polypeptide having antiviral activity.

In one aspect of the invention, methods for suppressing BLV-related lymphocyte proliferation are provided. In the methods, an amount of Shiga-toxin polypeptide effective to suppress BLV-related lymphocyte proliferation is administered. In one embodiment, a Shiga-toxin composition is administered to an animal subject in an amount effective to (1) prevent or treat BLV-induced persistent lymphocytosis, (2) to prevent or treat BLV-induced malignant lymphoma, (3) to eliminate BLV-expressing cells, (4) to slow the progression of BLV infection, or (5) to inhibit BLV transmission from infected to uninfected animals. The Shiga-toxin polypeptide includes the portion of the toxin that imparts antiviral activity to the polypeptide. In one embodiment, the Shiga-toxin polypeptide is the subunit A of Stx1. In another embodiment, the Shiga-toxin polypeptide is the Stx1 holotoxin.

Effective amounts of Shiga-toxin polypeptide generally include any amount sufficient to detectably suppress BLV-related lymphocyte proliferation by any of the assays described herein, by other assays known to those having ordinary skill in the art, or by detecting an alleviation of symptoms in a subject infected with BLV.

In one embodiment, the method provides a method for suppressing BLV-related cell proliferation by contacting cells with a Shiga-toxin polypeptide having antiviral activity. In the method, an amount of Shiga-toxin polypeptide effective to suppress BLV-related cell proliferation is administered.

The Shiga-toxin polypeptide can administered in several forms. In one embodiment, a Shiga-toxin polypeptide is administered in a purified form. In another embodiment, a Shiga-toxin polypeptide is provided by a probiotic microorganism. The microorganism can be either a naturally-occurring microorganism that expresses a Shiga-toxin polypeptide having antiviral activity, or a microorganism that has been modified to express a Shiga-toxin polypeptide having antiviral activity. The probiotic microorganism can be modified to express a Shiga-toxin polypeptide having antiviral activity that does not include the B subunit of the holotoxin. In another embodiment, a Shiga-toxin polypeptide is provided by a transgenic plant modified to express a Shiga-toxin polypeptide having antiviral activity.

In another aspect of the invention, compositions for delivering a Shiga-toxin polypeptide are provided. The Shiga-toxin polypeptide can be administered in a purified form along with an acceptable carrier. Alternatively, the Shiga-toxin polypeptide can be administered by way of an organism that expresses the polypeptide. In one embodiment, a Shiga-toxin polypeptide is produced by a probiotic microorganism modified to express a Shiga-toxin polypeptide having antiviral activity. In another embodiment, a Shiga-toxin polypeptide is produced by a plant modified to express a Shiga-toxin polypeptide having antiviral activity.

As used herein, the following terms have the meanings defined below:

The term "Shiga-toxin polypeptide" refers to a polypeptide from the Shiga-toxin type 1 family of ribosome-inactivating proteins having antiviral activity as measured by the suppression of proliferation of BLV-infected cells. These polypeptides can include a portion or all of either subunit A alone, or in combination with subunit B (e.g., the Stx1 holotoxin). The term also refers naturally occurring forms of Shiga-toxin polypeptides as well as modified derivatives thereof having antiviral activity. A partial Shiga-toxin polypeptide coding sequence will suffice for antiviral activity. A minimal essential coding sequence(s) for a functional Shiga-toxin polypeptide can be determined, for example, by synthesis and evaluation of subsequences comprising the native Shiga-toxin polypeptide, and by site-directed mutagenesis studies of the Shiga-toxin polypeptide coding sequence. Moreover, the term "Shiga-toxin polypeptide" includes fusion proteins in which Shiga-toxin polypeptide sequences are fused to heterologous sequences to improve levels of expression, stability, and the like.

The term "Shiga-toxin composition" refers to any composition containing a Shiga-toxin polypeptide having antiviral activity. For example, it includes Shiga-toxin polypeptides in partially or completely purified form, and in the form of a probiotic microorganism or a transgenic plant expressing a Shiga-toxin polypeptide. Anti-viral activity, may be determined using the assay for the suppression of spontaneous lymphocyte proliferation disclosed herein. The Shiga-toxin composition can include an acceptable carrier for effective delivery. The nature of the carrier can depend on the delivery method.

The term "probiotic microorganism" refers to a live microbial feed supplement which beneficially affects the host animal by improving its intestinal microbial balance (see Fuller 1989). Recent speculations suggest that "genetic engineering offers the possibility of using microbes to deliver specific actions or products to the colon or other mucosal surfaces . . . other fertile areas for future study include defining the mechanisms of action of various biotherapeutic agents with the possibility of applying genetic engineering to enhance activities" (Elmer et al. 1996). Elmer et al. (1996) further point out that the terms "probiotic" and "biotherapeutic agent" have been used in the literature to describe microorganisms that have antagonistic activity toward pathogens in vivo; those authors more specifically prefer the term "biotherapeutic agent" to denote "microorganisms having specific therapeutic properties." The present invention teaches a novel type of "probiotic" or "biotherapeutic" treatment using specifically engineered strains of microorganisms provided herein which do not occur in nature. Nonetheless, available teachings concerning selection of optimal microbial strains, in particular bacterial strains, for conventional probiotic or biotherapeutic applications can be employed in the context of the present invention.

The term "plant" refers to whole plants, plant organs (e.g., leaves, stems, flowers, roots, etc.), seeds and plant cells (including tissue culture cells), and progeny of same. The class of plants that can be used in the method of the invention is generally as broad as the class of higher plants amenable to transformation techniques, including both monocotyledonous and dicotyledonous plants, as well as certain lower plants such as algae. Suitable plants include plants of a variety of ploidy levels, including polyploid, diploid and haploid. The term "transgenic plant" refers to a plant modified to express a Shiga-toxin polypeptide.

The term "treatment" as used herein, refers to reducing or alleviating symptoms of BLV infection in a ruminant, preventing symptoms from worsening or progressing, inhibiting BLV expression of propagation, eliminating BLV-infected cells, or preventing the infection or symptom in a ruminant that is free therefrom. Thus, for example, treatment includes destruction of bovine leukemia viruses, inhibition of or interference with its expression or propagation, neutralization of its pathological effects and the like. As used herein, the term "treatment" also refers to prophylactic administration of a Shiga-toxin composition. A disorder is "treated" by partially or wholly remedying the cause of the disorder.

As noted above, the present invention provides methods and composition for the suppression of proliferation of BLV-infected lymphocytes using a Shiga-toxin polypeptide having antiviral activity. In one aspect of the invention, a Shiga-toxin polypeptide is provided to BLV-infected lymphocytes in cultures of peripheral blood mononuclear cells (PBMC) from infected cows.

Figure 1B:
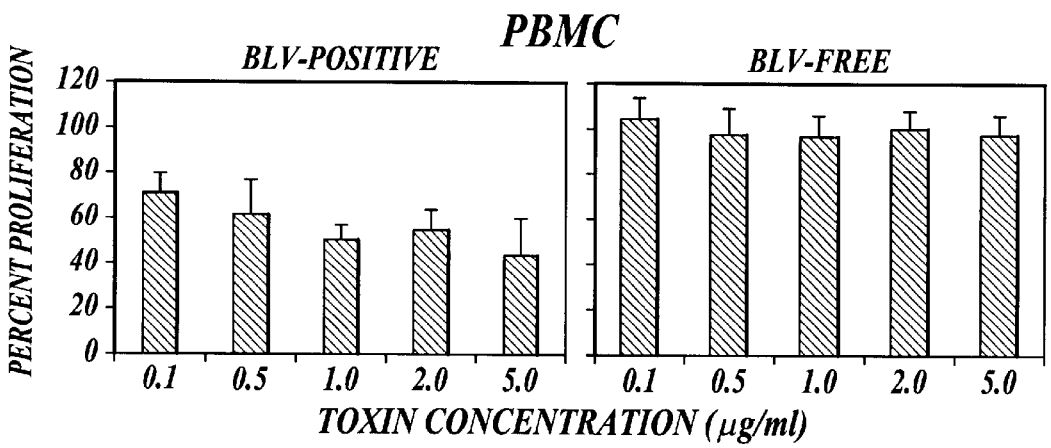
Figure 1C:
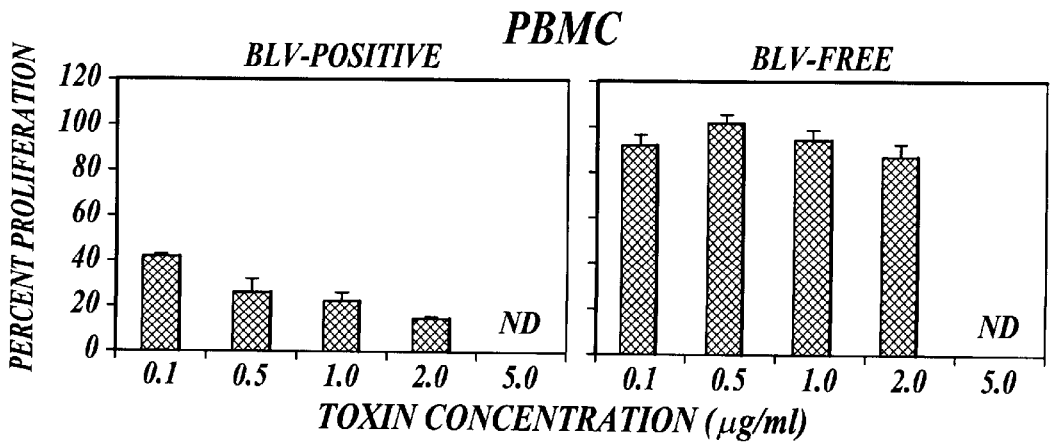
Figure 2A:
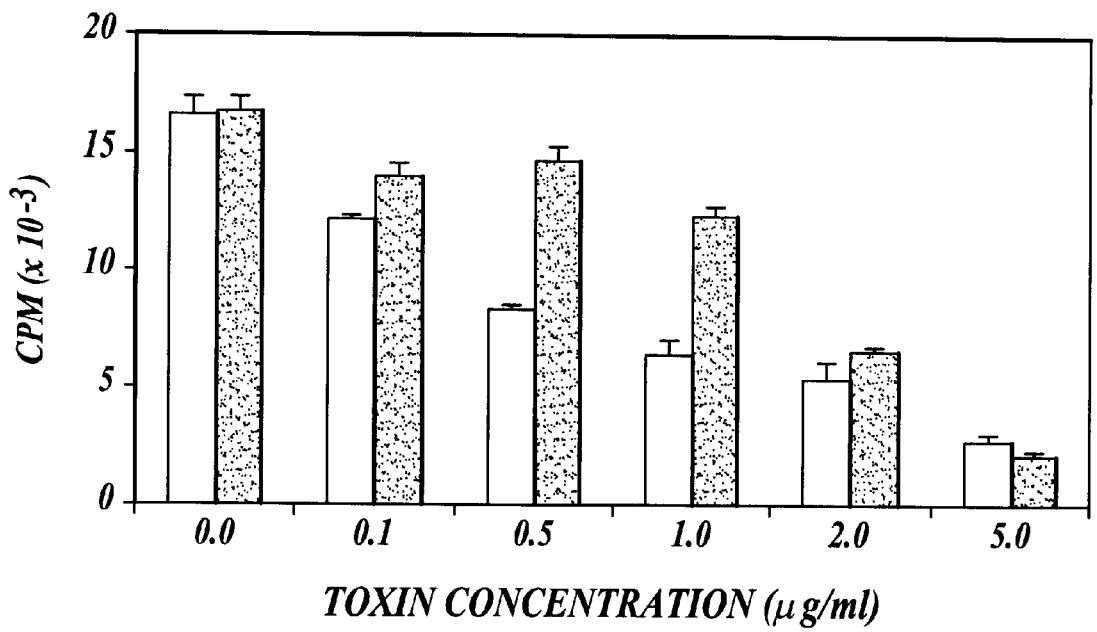
FIGS. 2A and 2B illustrate the effect of antitoxin on Stx1-mediated inhibition of SLP in PBMC cultures from persistently lymphocytic (BLV-positive) cows. PBMC from BLV-positive cows were incubated with varying concentrations of toxin (A, A subunit; B, holotoxin,) without anti-Stx1A (open bars) and with anti-Stx1A diluted 1:100 (stippled bars). Cell proliferation was measured as incorporation of tritiated thymidine and expressed as counts per minute (CPM). Data are means±SE from four replicates from a representative experiment. ND refers to not done.
Figure 2B:
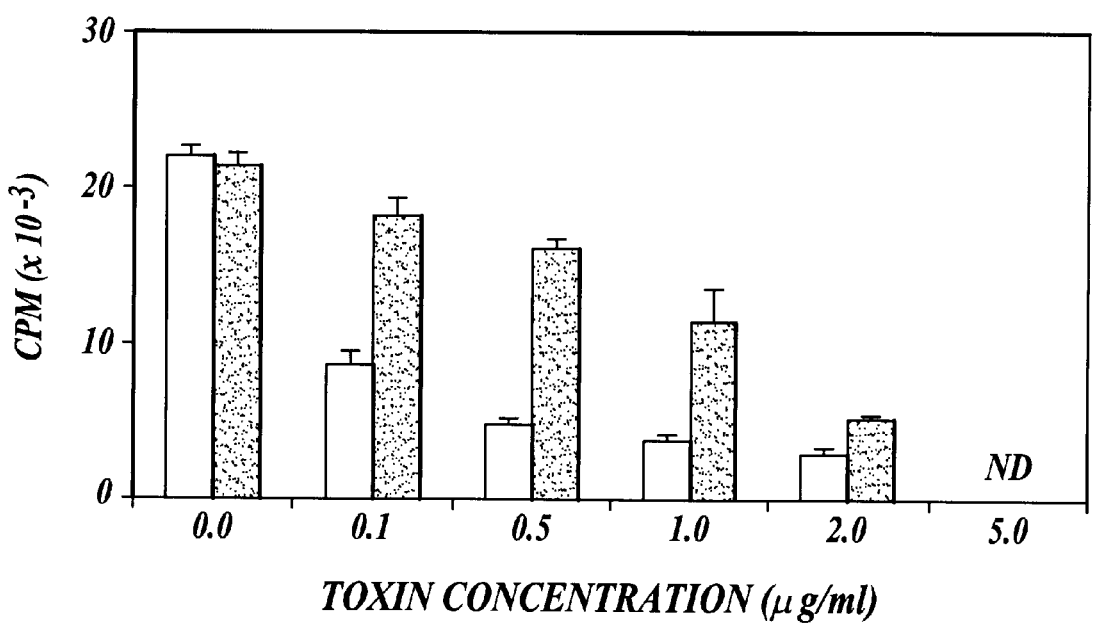

PBMC from five BLV-positive cows in the persistently lymphocytotic stage of infection invariably proliferated in vitro, and this SLP was consistently suppressed by Stx1 (FIG. 1). Holotoxin or the A subunit alone (Stx1A) were potent suppressors of SLP, acting in a dose-dependent manner over the range of concentrations tested. Compared to Stx1A, the B subunit (Stx1B) was far less potent in suppressing SLP even with molar concentrations of Stx1B more than 4-fold higher than Stx1A. Moreover, in contrast to Stx1A, Stx1B did not act in a dose-dependent fashion. Anti-Stx1A immune serum neutralized Stx1 or Stx1A activity in a dose-dependent manner (FIG. 2) and did not affect cellular proliferation in cultures without toxin. The result confirms that that the suppression was due to Stx1 and not due to some spurious inhibitor present in the toxin preparations.

In contrast to SLP, proliferation of BLV-free PBMC induced by poke weed mitogen was only weakly sensitive to Stx1 (FIG. 1). Moreover, the suppression of SLP by Stx1 did not diminish the ability of B-cells in BLV-positive PBMC cultures to respond to immunostimulation by interleukin-2 or poke weed mitogen (Table 1). Especially relevant is the fact that Stx1 was a potent SLP inhibitor at low concentrations, which had only marginal impact on normal PBMC. The result implies that Stx1 suppresses SLP via a selective mechanism and is consistent with the fact that very few B cells in BLV-infected cattle express viral proteins or viral particles (Gupta et al. 1984).

Figure 3A:
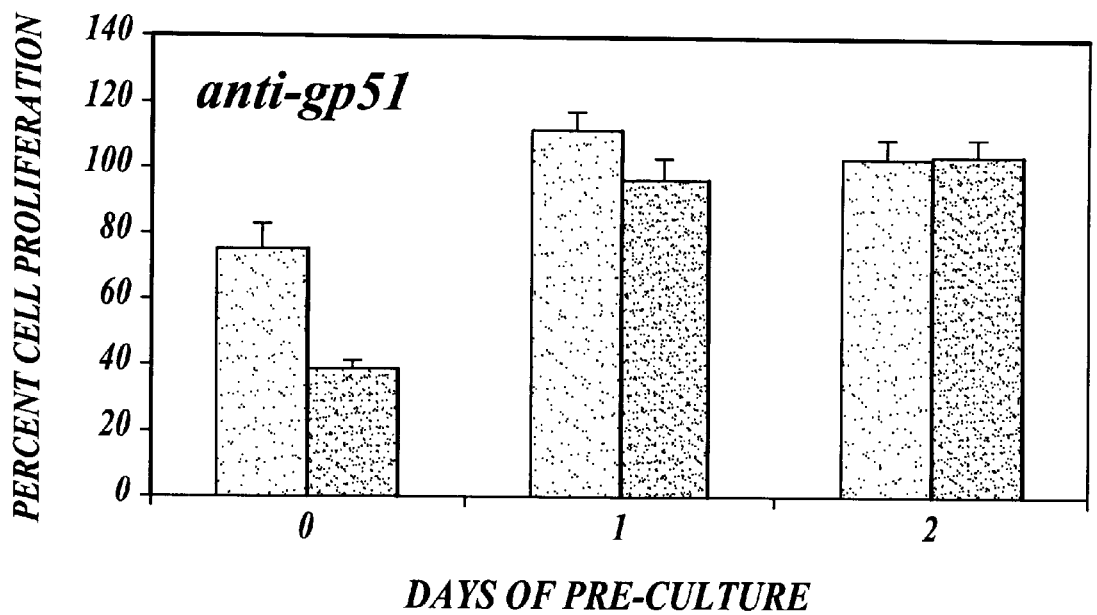
FIG. 3 illustrates the effect of pre-culture on the ability of anti-BLV antibody or the Stx1 subunits to inhibit SLP in cultures of PBMC from persistently lymphocytotic (BLV-positive) cows. Anti-gp51 monoclonal antibody or toxins were added to PBMC cultures on day 0 (without pre-culture) or after PBMC had been precultured for 1 or 2 days in medium. Antibody was applied at 2.0 $\mu$g/ml (light stipple) and 20.0 $\mu$g/ml (dark stipple). Toxins were applied at 0.1 $\mu$g/ml (light stipple) and 1.0 $\mu$g/ml (dark stipple). Cell proliferation was measured as incorporation of tritiated thymidine and expressed as a percentage of the cell proliferation in control cultures treated with PBS. Data are means±SE from three or more experiments.
Figure 3B:
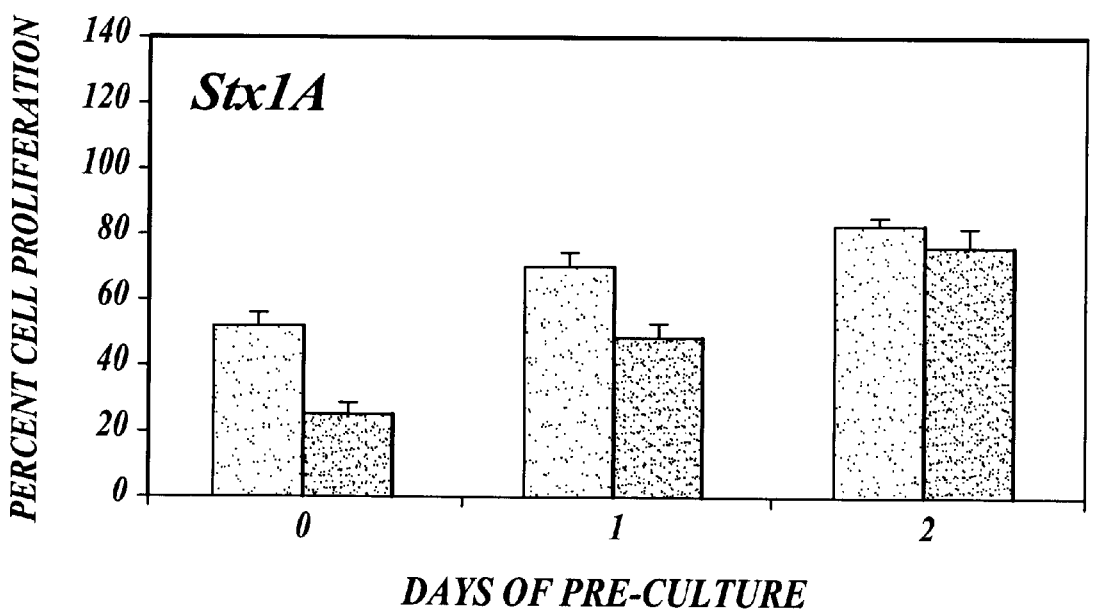

SLP in cultures of BLV-positive PBMC is preceded within 24 hr of culture by de novo synthesis of viral proteins and dissemination of viral particles (Baliga & Ferrer 1977). The expression of BLV particles in culture reaches maximum after 12 to 24 hr of cell culture (Zandomeni et al. 1992). It is known that anti-BLV serum can block SLP (Thorn et al. 1981; Trueblood et al. 1998). This possibly results from the interference with the release of BLV particles from cultured cells (Driscoll et al. 1977). To assess whether viral proteins accessible to antibody were required to sustain SLP, the ability of antiviral antibody to interfere with SLP over a two-day period was examined. Antiviral antibody was able to reduce thymidine incorporation in spontaneously proliferating cultures by 60% (FIG. 3). However, this inhibition required application of antiviral antibody at the beginning of cell culture (FIG. 3). These results are in agreement with the findings that dissemination of BLV proteins is involved in initiation of SLP, but the results also suggest that BLV proteins are not required for continuation of an established SLP event. Similar to treatment with antiviral antibody, the ability of Stx1A to inhibit SLP was reduced when cells were precultured in medium for 24 hours before toxin application (FIG. 3). These results indicate that inhibition of SLP by Stx1A is time-dependent, and may be based on the ability of the toxin to interfere with the initiation of spontaneous proliferation. The fact that susceptibility of SLP to inhibition by either Stx1A or antiviral antibody lessens within 24 hours of culture evidences that the cells involved in dissemination of viral proteins and the initiation of SLP constitute targets for Stx1.

Figure 4:
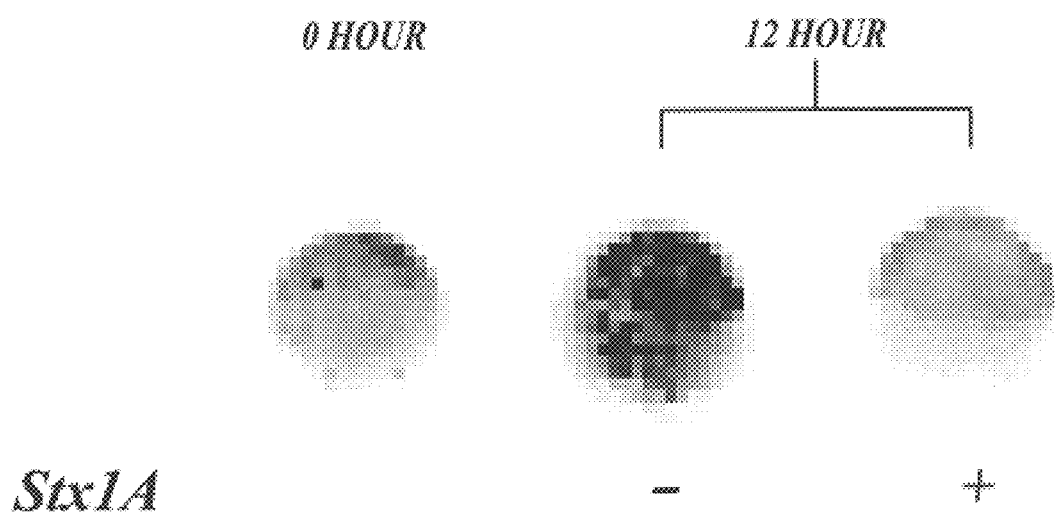
FIG. 4 illustrates the effect of Stx1A on the expression of BLV protein in cultured PBMC from BLV-positive cows. PBMC were harvested after 12 hr of culture with or without 1.0 $\mu$g/ml Stx1A, washed cells were lysed and blotted onto nitrocellulose. The blot was probed with monoclonal antibody against BLV p24 core protein. Sample obtained prior to culture (0 hr) shows p24 protein in unstimulated ex vivo PBMC.

The expression of BLV p24 core protein in PBMC cultured with Stx1A was significantly reduced. Analysis of cell lysates of PBMC cultured for 12 hr showed a 442-fold reduction in the amount of p24 protein in cells treated with toxin compared to cells in the control cultures without toxin (FIG. 4). The reduced expression of BLV p24 protein in cell cultures treated with Stx1 could be due either to the nonlethal suppression of viral protein synthesis or Stx1-mediated lysis of the cells expressing viral proteins.

In summary, these results demonstrate that SLP of BLV-positive PBMC is suppressed by Stx1 and that the inhibitory effect is mediated by the A subunit of holotoxin. These results provide a demonstration of both the antiviral activity of Stx, and the suppression of BLV expression and BLV-associated cell proliferation by this family of toxins. Moreover, the results are consistent with previous research showing that other members of the RIP family of toxins possess antiviral activity against specific viruses (reviewed in Stirpe et al. 1992).

The most likely explanation for the inhibitory effect is that Stx1 has an adverse impact on the cells that express the virus. Very little information exists regarding the action of Stx1 on bovine cells. A recent publication (Menge et al. 1999) describes the impact of Stx1 on the metabolic rate of normal bovine PBMC. The study showed that the metabolism of PBMC was reduced by Stx1A but only if the cultures were first stimulated by mitogens. Menge et al. (1999) did not detect any cytotoxic impact of Stx1 on PBMC, even when Stx1 caused 50% reduction of the metabolic rate. The reference does not clarify the BLV status of their PBMC donors, it is possible that the effects observed were due to antiviral activity of Stx1. Additional details of this aspect of the invention are described in Example 1. A sequence coding for a Shiga-toxin polypeptide of the present invention can be inserted ex vivo into cells previously removed from a given animal. Such transformed autologous or homologous host cells, reintroduced into the animal or human, will express directly the corresponding Shiga-toxin polypeptide in vivo. The feasibility of such a therapeutic strategy to deliver a therapeutic amount of an agent in close proximity to the desired target cells and pathogens (e.g., to the virus, more particularly to the retrovirus, specifically to HIV and its envelope glycoprotein gp120), has been demonstrated in studies with cells engineered ex vivo to express sCD4 (Morgan et al., 1994).

The present invention also provides methods and compositions for suppressing BLV-related lymphocyte proliferation by administering a Shiga-toxin polypeptide to a ruminant. BLV infections in cattle are chronic and, in most animals, the disease does not progress to the malignant stage. Although antibodies to BLV are clearly important in viral repression (Portetelle et al. 1980; Bruck et al. 1994), they do not always prevent progression of BLV infection to the PL and malignant stages. Consequently, other factors interfering with BLV replication may play a role in a suppression of this virus. The effect of Stx1 on SLP provides strong support for the premise that Shiga-toxin polypeptides serve a protective role in BLV-infected cows. Gastrointestinal Shiga-toxin producing *Escherichia coli* (STEC) release toxin systemically because cattle have anti-Stx antibodies in serum and colostrum (Pirro et al. 1995). More evidence to support the movement of the toxin out of the gastrointestinal tract comes from tissue culture experiments. Biologically active Stx1 is capable of moving across a monolayer of the intact polarized human intestinal epithelial cells (Acheson et al. 1996). Therefore, Stx1 administered to ruminants in their feed should be capable of crossing the intestine. Stx1 is not cytotoxic to normal bovine PBMC (Menge et al. 1999) and, consequently, the presence of Stx in tissues or body fluids of cattle harboring BLV could benefit these animals, for example, by causing deletion of the BLV-expressing cells, by inhibiting viral expression and propagation, or by inhibiting the transmission of BLV between animals.

Thus, in another embodiment, the invention provides a method for treating a BLV-related disorder in a ruminant. In the method, an amount of a Shiga-toxin composition effective to suppress BLV-related cell proliferation is administered to the ruminant. The BLV-related disorder can include persistent lymphocytosis, malignant lymphoma, and the progression of viral infection.

As noted above, in another aspect, the invention provides Shiga-toxin compositions. In one embodiment, the composition includes an amount of a Shiga-toxin polypeptide effective to suppress BLV-related lymphocyte proliferation in an animal subject when administered to the animal. The composition can further include an acceptable carrier.

In addition to partially and fully purified Shiga-toxin polypeptides, the compositions of the invention include a probiotic microorganism that has been modified to express a Shiga-toxin polypeptide having antiviral activity. Any expression vector containing replicon and control sequences that are derived from species compatible with the host cell may be used in the practice of the invention. The term "expression vector" refers to a piece of DNA, usually double-stranded, which may have inserted into it a piece of heterologous DNA. The vector or replicon may be, for example, of plasmid or viral origin. Vectors contain sequences that facilitate the autonomous replication of the vector in a host cell. The term "replicon" in the context of this disclosure also includes sequence regions that target or otherwise facilitate the recombination of vector sequences into a host chromosome. The vector is used to transport the heterologous DNA into a suitable host cell. Heterologous DNA is defined as DNA not naturally found in the host cell. In the context of the present invention, heterologous DNA includes coding sequences for Shiga-toxin polypeptides and selectable markers used to screen for successful introduction of the expression vector into the host cell. Once in the host cell, the expression vector can replicate independently of, or coincidental with, the host chromosomal DNA, and several copies of the vector including the heterologous DNA may be generated. Alternatively, the expression vector may target the insertion of the heterologous DNA into a host chromosome. In addition, the vector also contains the necessary elements that permit transcription of the heterologous DNA into a mRNA molecule or otherwise cause replication of the heterologous DNA into multiple copies of RNA. Some expression vectors additionally contain sequence elements adjacent to the inserted foreign DNA that allow translation of the mRNA into a protein molecule. Many molecules of the mRNA and polypeptide encoded by the heterologous DNA can thus be rapidly synthesized.

The terms "transformation" and "transformed cell" refer to the introduction of DNA into a cell. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCl18, pUC119, and Bluescript M13, all of which have been described (Sambrook et al. 1989). However, many other suitable vectors are available as well. These vectors contain genes coding for ampicillin and/or tetracycline resistance which enables cells transformed with these vectors to grow in the presence of these antibiotics.

The promoters most commonly used to achieve expression in prokaryotic vectors include the β-lactamase (penicillinase) and lactose promoter systems (Itakura et al. 1977; Chang et al. 1978; Goeddel et al. 1979) and a tryptophan (trp) promoter system (Goeddel et al. 1980), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al. 1980). Prokaryotic host cells or other host cells with rigid cell walls are preferably transformed using the calcium chloride method (Sambrook et al. 1989). Alternatively, electroporation may be used for transformation of these cells. Several techniques for the transformation of prokaryotes can be used (Hanahan 1991).

A representative method for expressing Stx1A in a probiotic microorganism is described in EXAMPLE 2. Those skilled in the art will recognize that various modifications can be made to the methods and genes described herein while not departing from the spirit and scope of the present invention. For example, in order to circumvent the potential cytotoxicity of cytoplasmic accumulation of a Shiga-toxin polypeptide, probiotic microorganisms may be manipulated to secrete these polypeptides.

In another embodiment, the present invention provides a naturally-occurring probiotic microorganism that expresses a Shiga-toxin having antiviral activity and that has been modified to eliminate expression of the B subunit of the holotoxin. One skilled in the art will recognize various approaches for deleting the B subunit from the microorganism, for example, by using homologous recombination as described in Schulz et al. (1997).

In a further embodiment, the invention provides a transgenic plant that has been modified to express a Shiga-toxin polypeptide having antiviral activity. Suitable plants include tobacco and *Chenopodium quinoa,* among others. The genetic information required for expression of a Shiga-toxin polypeptide having antiviral activity is introduced into plants using a plant expression vector, which contains the necessary elements to stably integrate a gene to be expressed in plants and passed on to its progeny. As used herein, the term "gene" refers to an element or combination of elements that are capable of being expressed in a cell, either alone or in combination with other elements. In general, a gene comprises (from the 5' to the 3' end): (1) a promoter region, which includes a 5' nontranslated leader sequence capable of functioning in plant cells; (2) a gene or DNA sequence, which codes for the desired protein; and (3) a 3' nontranslated region, which typically causes the termination of transcription and the polyadenylation of the 3' region of the RNA sequence. Each of these elements is operably linked by sequential attachment to the adjacent element. A gene comprising the above elements may be inserted by standard recombinant DNA methods into a plant expression vector.

The segment of DNA referred to as the promoter is responsible for the regulation of the transcription of DNA into mRNA. A number of promoters which function in plant cells are known in the art, and may be employed in the practice of the present invention. These promoters may be obtained from a variety of sources such as plants or plant viruses, and may include, but are not limited to, promoters isolated from the caulimovirus group such as the cauliflower mosaic virus 35S promoter (CaMV35S), the enhanced cauliflower mosaic virus 35S promoter (enh CaMV35S), the figwort mosaic virus full-length transcript promoter (FMV35S), and the promoter isolated from the chlorophyll a/b binding protein. The nontranslated leader sequence can be derived from any suitable source and can be specifically modified to increase the translation of the mRNA. The 5' nontranslated region can be obtained from the promoter selected to express the gene, the native leader sequence of the gene or coding region to be expressed, viral RNAs, suitable eucaryotic genes, or a synthetic gene sequence. The termination region or 3' nontranslated region is employed to cause the termination of transcription and the addition of polyadenylated ribonucleotides to the 3' end of the transcribed mRNA sequence. The termination region may be native with the promoter region, native with the gene, or may be derived from another source, and would preferably include a terminator and a sequence coding for polyadenylation. Suitable 3' nontranslated regions of the chimeric plant gene include, but are not limited to: (1) the 3' transcribed, nontranslated regions containing the polyadenylation signal of Agrobacterium tumor-inducing (Ti) plasmid genes, such as the nopaline synthase (NOS) gene, and (2) plant genes like the soybean 7S storage protein genes and the pea small subunit of the ribulose 1,5-bisphosphate carboxylase-oxygenase.

The addition of appropriate introns and/or modifications of coding sequences for increased translation can also substantially improve transgene expression. Appropriate introns can include but are not limited to the maize hsp70 intron, maize adh 1 intron, and rice actin intron. Therefore, to select a vector for expression of a Shiga-toxin polypeptide, constructs containing various combinations of promoters and expression enhancement elements can be introduced into plant cells.

The most common method of plant transformation is performed by cloning a target transgene into a plant transformation vector that is then transformed into *Agrobacterium tumifaciens* containing a helper Ti-plasmid (Hoeckema et al. 1983). The Agrobacterium cells containing the expression vector are incubated with leaf slices of the plant to be transformed (An et al. 1986, see also Hooykaas 1989). Transformation of cultured plant host cells is normally accomplished through *Agrobacterium tumifaciens*. Cultures of host cells that do not have rigid cell membrane barriers are usually transformed using the calcium phosphate method or other methods for introducing DNA into cells such as Polybrene, protoplast fusion, electroporation, and direct microinjection into nuclei.

In addition to the methods described above, a large number of methods are known in the art for transferring cloned DNA into a wide variety of plant species, including gymnosperms, angiosperms, monocots and dicots. Plant transformation strategies and techniques are reviewed in Birch (1997) and Forester (1997). Minor variations make these technologies applicable to a broad range of plant species. In the case monocot transformation, particle bombardment appears to be the method of choice for most commercial and university laboratories. However, monocots such as maize can also be transformed by using Agrobacterium transformation methods as described in U.S. Pat. No. 5,591,616. The use of whiskers for the transformation of plant cells, particularly maize, is described in U.S. Pat. No. 5,464,765. Methods of transforming and regenerating soybean are described in U.S. Pat. No. 5,968,830. U.S. Patent No. 5,969,215 describes transformation techniques for producing transformed *Beta vulgaris* plants, such as the sugar beet.

Each of the above transformation techniques has advantages and disadvantages. In each of the techniques, DNA from a plasmid is genetically engineered such that it contains not only the gene of interest, but also selectable and screenable marker genes, for example, the kan gene encoding resistance to kanamycin. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest. Transformed plant calli may be selected through the selectable marker by growing the cells on a medium containing, for example, kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

Traditional Agrobacterium transformation with antibiotic resistance selectable markers is problematical because of public opposition that such plants pose an undue risk of spreading antibiotic tolerance to animals and humans. Such antibiotic markers can be eliminated from plants by transforming plants using the Agrobacterium techniques similar to those described in U.S. Pat. No. 5,731,179. Antibiotic resistance issues can also be effectively avoided by the use of bar or pat coding sequences, such as is described in U.S. Pat. No. 5,712,135. These preferred marker DNAs encode second proteins or polypeptides inhibiting or neutralizing the action of glutamine synthetase inhibitor herbicides phosphinothricin (glufosinate) and glufosinate ammonium salt.

There are numerous factors which influence the success of transformation. The design and construction of the expression vector influence the integration of the heterologous sequence into the chromosomal DNA of the plant nucleus and the ability of the transgene to be expressed by the cell. A suitable method for introducing the expression vector into the plant cell nucleus in a nonlethal manner is preferred. Importantly, the type of cell into which the construct is introduced must, if whole plants are to be recovered, be of a type which is amenable to regeneration, given an appropriate regeneration protocol. A representative method for preparing a transgenic plant expressing a Shiga-toxin polypeptide is described in Example 3.

A transgenic plant of the present invention expressing a Shiga-toxin polypeptide having antiviral activity can be cultivated using methods known to those of ordinary skill in the art. The presence of a Shiga-toxin gene, or gene product, in the transformed plant may be determined by any suitable method known to those skilled in the art. Included in these methods are Southern, northern, and western blot techniques, ELISA, and bioassays. A representative assay for determining the presence of a Shiga-toxin gene or gene product in the transformed plant is described in Example 3.

The transgenic plants of the present invention can be further propagated to generate genetically true-breeding populations of plants possessing the modulated cell division trait. Further, the transgenic plants can be crossed with other plant varieties, having one or more desirable phenotypic traits, such as, for example, stress and pest resistance or nutritional and taste quality, to generate novel plants possessing the aforementioned desirable traits in combination with the transgenic trait that modulates cell division.

In one embodiment of the method of the invention, a composition including a Shiga-toxin polypeptide having antiviral activity is administered to a ruminant in an amount effective to eliminate BLV-infected cells and/or to prevent the expression and propagation of BLV. Shiga-toxin polypeptides that are nontoxic to humans and other animals, such as Stx1A, are preferred.

There are several ways in which a Shiga-toxin polypeptide can be administered to a ruminant. For example, a Shiga-toxin composition can be administered in a variety of ways including oral, rectal, intranasal and intravenous. The composition containing the Shiga-toxin polypeptides can be in any form suitable for the intended method of administration, including, for example, a solution, a suspension, or an emulsion. The composition can also be administered as an admixture with a suitable carrier or diluent. Such an admixture can be prepared according to conventional compounding techniques. The carrier may take a wide variety of forms depending on the form of preparation desired for administration. Suitable carriers include processing agents and drug delivery modifiers and enhancers, such as, for example, calcium phosphate, magnesium stearate, talc, monosaccharides, disaccharides, starch, gelatin, cellulose, methyl cellulose, sodium carboxymethyl cellulose, dextrose, hydroxypropyl-β-cyclodextrin, polyvinyl-pyrrolidinone, low melting waxes, ion exchange resins, and the like, as well as combinations of any two or more thereof.

Liquid carriers are typically used in preparing solutions, suspensions, and emulsions. Liquid carriers for use in the practice of the present invention include, for example, water, saline, acceptable organic solvent(s), acceptable oils or fats, and the like, as well as mixtures of two or more thereof. The liquid carrier can contain other suitable additives such as solubilizers, emulsifiers, nutrients, buffers, preservatives, suspending agents, thickening agents, viscosity regulators, stabilizers, and the like.

Compositions of the present invention can also be in the form of microparticles, microcapsules, liposomal encapsulates, and the like, as well as combinations of any two or more thereof. Solid dosage forms for oral administration can include capsules, tablets, pills, powders, and granules. In such solid dosage forms, the Shiga-toxin composition may be admixed with at least one inert diluent such as sucrose, lactose, or starch. Such dosage forms may also comprise additional substances other than inert diluents, for example, lubricating agents such as magnesium stearate. In the case of pills, capsules, and tablets, the dosage forms can also comprise buffering agents. Tablets and pills can be prepared with enteric coatings.

The Shiga-toxin compositions of the present invention are administered in a therapeutically effective dose. A therapeutically effective dose can be determined by a variety of methods. For example, an effective dose can be determined by in vitro experiment followed by in vivo studies. The amount of Shiga-toxin composition that can be combined with a carrier to produce a single dosage form will vary depending upon the specific composition, the animal treated, and the administration mode. The specific dose level for any particular animal will depend upon a variety of factors including the antiviral activity of the composition employed, the age, body weight, general health, sex, diet, time of administration, administration route, excretion rate, and the severity of the BLV-related disease in the animal.

In one embodiment of the invention, the Shiga-toxin polypeptide is delivered to the ruminant in a purified or partially purified form. A representative method for Shiga-toxin polypeptide purification is described in Example 1. There are a variety of modes of administration of pure or partially purified composition of a Shiga-toxin polypeptide to a ruminant. Suitable modes of administration include enteral, intramuscular, transmucosal, intravenous, intranasal, rectal, and the like.

In another embodiment of the invention, the Shiga-toxin polypeptide can be delivered to the ruminant through the administration of a probiotic microorganism that produces a Shiga-toxin polypeptide. There are a variety of probiotic microorganisms suitable for use in this invention including E. coli, Aeromonas, and Citrobacter. It will be appreciated that other suitable microorganisms that are harmless to ruminants can be used.

In the method of the invention, a Shiga-toxin composition is administered to suppress BLV-related lymphocyte proliferation. In one embodiment, the administered composition includes a naturally occurring probiotic microorganism that expresses a Shiga-toxin polypeptide. Suitable microorganisms can include E. coli. For example, there are more than 100 serotypes of E. coli that produce Shiga-toxin, most of which have been shown not to be human pathogens. In another embodiment, the composition includes a probiotic microorganism that expresses a Shiga-toxin that has been modified to eliminate expression of the B subunit of the holotoxin. In a further embodiment, a Shiga-toxin polypeptide is provided in the form of a probiotic organism that has been genetically modified to express the polypeptide.

Administration of a probiotic microorganism can be accomplished by any suitable method for introducing the organism into the digestive tract. The microorganism can be mixed with a carrier and applied to liquid or solid feed or to drinking water. The carrier is preferably nontoxic to the microorganism and the animal. Preferably, the carrier includes one or more ingredients that promote the viability of the microorganism during storage. The microorganism can also be formulated as an inoculant paste to be directly injected into an animal's mouth. The formulation can include other ingredients to improve palatability, improve shelf-life, impart nutritional benefits, and the like. If a reproducible and measured dose is desired, the microorganism can be administered by a rumen cannula, as described in U.S. Pat. No. 5,965,128. The amount of probiotic microorganism to be administered is governed by factors affecting efficacy.

In another embodiment of the invention, a Shiga-toxin polypeptide having antiviral activity can be delivered to the ruminant in the form of a transgenic plant expressing a Shiga-toxin polypeptide. Administration of a transgenic plant expressing a Shiga-toxin polypeptide can be accomplished by any suitable method for introducing the plant into the digestive tract. For example, the transgenic plant, or part thereof, can be administered in a fresh or dried form. The transgenic plant can also be mixed with a carrier and applied to liquid or solid feed or to drinking water. The carrier material is preferably nontoxic to the plant and the animal. Preferably, the carrier contains one or more ingredients that promote the preservation of the Shiga-toxin polypeptide during storage. Plant material can also be formulated as an inoculant paste to be directly injected into an animal's mouth. The formulation can include other ingredients to improve palatability, improve shelf-life, impart nutritional benefits, and the like.

The following examples are provided for the purposes of illustrating, and not limiting, the present invention.

EXAMPLES

Example 1

Suppression of Bovine Leukemia Virus Spontaneous Lymphocyte Proliferation by Stx1

In this example, the suppression of BLV-related spontaneous lymphocyte proliferation by administering purified Stx1 holotoxin and Stx1 subunit A is described.

Materials and Methods. Freisian-Holstein cows from the University of Idaho dairy were used as blood donors. Cows were identified as BLV-positive by high titers of anti-BLV antibody. Five persistently lymphocytotic (PL) cows were identified by elevated numbers and percentages of B cells (three standard deviations above normal levels) in peripheral circulation and used as BLV-positive donors. Cows with no detectable anti-BLV antibodies were used as BLV-negative donors.

Blood was collected by jugular venipuncture into acid-citrate-dextrose (ACD) (one part to four parts whole blood). PBMC were purified by density gradient centrifugation using Accu-Paque (Accurate Chemical and Scientific Corp., Westbury, N.Y.) (1.086 g/ml) as previously described (Ferens et al. 1998). Erythrocytes were lysed by incubation in warm ammonium chloride, and PBMC preparation was washed several times in PBS/ACD mix (4:1) to remove platelets. PBMC were cultured in 96-well culture plates (Corning) at the initial density of $2.5 \times 10^6$ cells/ml ($0.5 \times 10^6$ cells/well) in RPMI-1640 with 20% heat-inactivated fetal bovine serum, 2 mM L-glutamine, 100 units/ml penicillin and 100 $\mu$g/ml streptomycin. To assay cell proliferation, 3H-thymidine was added to the wells (1.0 μCi/well) 48 hr after the start of cell culture and 16–18 hr prior to cell harvest. Cells were harvested on a semiautomated 96-well plate harvester (Skatron Inc., Sterling, Va.) and the amount of 3H-thymidine incorporated was determined by liquid scintillation spectroscopy (Packard Instrument Co., Downers Grove, Ill.) and expressed as counts per minute (CPM). In all experiments measurements were obtained in at least four replicate samples. The percentage inhibition of proliferation was expressed as (CPM of cultures with toxin/CPM of control cultures without toxin)×100.

Recombinant Shiga toxin 1 (Stx1) A and B subunits were purified as previously described (Zollman, et al. 1994; Austin & Hovde 1995). Briefly, Stx1A was purified from $E.\ coli$ SY327(pSC25). Concentrated periplasmic proteins were adsorbed to Matrex Gel Green A agarose (Amicon) equilibrated with 10 mM PBS and Stx1A eluted as a single protein peak with approximately 0.3 M NaCl in a 0.15–1.0 M NaCl gradient. Stx1B was purified from $E.\ coli$ JM105 (pSBC32). Periplasmic proteins were fractionated by ammonium sulfate precipitation and Stx1B was separated by isoelectric focusing and native polyacrylamide gel electrophoresis. Holotoxin was reconstituted in vitro by combining Stx1A and Stx1B in 1:10 molar in 10 mM Tris HCl (pH 7.0) and dialyzed against 10 mM Tris-HCl (pH 7.0). The association of A and B subunits was confirmed by immunoblot of proteins separated by analytical discontinuous native-polyacrylamide gel electrophoresis. Before use in cultures, toxins were dialyzed exhaustively against 10 mM PBS and concentrations were measured using a Bio-Rad assay with bovine albumin as a standard.

To measure BLV expression, PBMC suspended at the initial density of $2.5 \times 10^6$ cells/ml were placed in culture dishes (4.0 ml per dish) without toxin or with 1.0 μg/ml Stx1 A. The cells were harvested at 12, 18, 24, 48, and 72 hr; centrifuged, and resuspended in 0.5 ml of 0.1 M Tris buffer (pH 7.5) with 0.1 M ethylenediamine-tetraacetic acid and 0.1 M phenylmethylsulfonyl fluoride. Samples were subjected to repeated freeze-thaw cycles until cells were lysed, as determined microscopically. Supernatant was transferred to nitrocellulose using a 96-well blotter, and cell lysates were probed with the murine monoclonal antibody BLV-3 against the BLV 24 kDa protein referred to throughout as anti-p24, and antimouse antibody conjugated to alkaline phosphatase (Sigma, St. Louis, Mo.). Immunoblots were developed using 5-bromo-4-chloro-3-indolyl phosphate (BCIP) and nitro blue tetrazolium (Sigma, St. Louis, Mo.) as substrate, according to manufacturer's instruction, scanned using Hewlett-Packard densitometer, and the results were quantitated using Molecular Analyzer analytical program. The cultures of BLV-negative PBMC served as negative controls.

Concanavalin A (ConA) and pokeweed mitogen (PWM) were purchased from Sigma (St. Louis, Mo.). Human recombinant interleukin-2 (IL-2) was purchased from Gibco, BRL (Grand Island, N.Y.). Polyclonal antibody to Stx1A was generated by standard technique in New Zealand white rabbits. Lipopolysaccharide (LPS) of $Salmonella\ typhimurium$ was purchased from DIFCO Laboratories (Detroit, Mich.). Murine monoclonal antibodies BLV-1 against the 51 kDa glycoprotein of BLV (referred to throughout as antigp51), and control antibody COLIS69A of the same isotype (IgG1) were purchased from WSU Monoclonal Antibody Center (Pullman, Wash.).

The results are presented as arithmetic means±standard errors (SE). In all experiments measurements were made from four or more replicates. Unless otherwise stated, the results are means of three or more experiments. Analysis of variance (ANOVA) was used to establish statistical significance at $p \leq 0.05$.

Stx1 suppresses SLP in cultures of PBMC from BLV-infected cows. PBMC from five BLV-positive cows in the persistently lymphocytotic stage of infection invariably proliferated in vitro, and this SLP was consistently suppressed by Stx1 (FIG. 1). Holotoxin or the A subunit alone (Stx1A) were potent suppressors of SLP, acting in a dose-dependent manner over the range of concentrations tested. The effects of Stx1A or holotoxin were significantly different at 0.1 and 0.5 μg/ml because the 95% confidence intervals of the percent proliferation values did not overlap. Compared to Stx1A, the B subunit (Stx1B) was far less potent in suppressing SLP even with molar concentrations of Stx1B more than 4-fold higher than Stx1A. Moreover, in contrast to Stx1A, Stx1B did not act in a dose-dependent fashion. The 95% confidence intervals of the percent proliferation values were overlapping for all concentrations of Stx1B.

Cellular proliferation in spontaneously proliferating cultures of BLV-positive PBMC almost exclusively involves B lymphocytes (Esteban et al. 1985; Jensen et al. 1990; Mirsky et al. 1996). Thus, to evaluate Stx1 activity on normal B cells, Stx1 inhibition of poke weed mitogen (PWM)-induced proliferation of normal BLV-free PBMC was measured because PWM primarily stimulates B cells. In contrast to SLP, PWM-induced proliferation of BLV-free PBMC was only weakly sensitive to Stx1 (FIG. 1). Low doses of Stx1A or Stx1 (0.1 μg/ml), sufficient to reduce SLP by 45% and 60%, respectively, caused <10% inhibition of proliferation induced by PWM. Stx1A at the highest concentration tested inhibited the PWM-induced proliferation by only 30%, whereas Stx1B or holotoxin were either marginally inhibitory or had a weak stimulatory effect in cultures from some donors.

To determine whether bovine T lymphocytes constitute targets for Stx1, the impact of Stx1 on PBMC proliferation induced by Concanavalin A (ConA) was tested. ConA is a lectin that induces T-cell proliferation by specific interaction with the T-cell receptor complex. T-cell proliferation induced by ConA was not affected by Stx1 holotoxin or toxin subunits.

These results indicate that SLP of BLV-positive PBMC is susceptible to Stx1-mediated inhibition, and that the inhibitory effect is mediated by the A subunit of holotoxin. Subsequent experiments to further characterize toxin activity were performed with purified Stx1A or B subunits.

BLV positive PBMC treated with Stx1A retain responsiveness to immunostimulation. To assess whether the toxin was selectively targeting SLP or indiscriminately suppressing the ability of BLV-positive PBMC to respond to immunostimulation, the impact of Stx1A on cellular proliferation was tested in cultures of BLV-positive PBMC supplemented with IL-2, a potent B-cell activator. The addition of 1.0 ng/ml of IL-2 to BLV-positive cultures strongly augmented proliferation, evidenced by a gain of about $6.0 \times 10^4$ CPM per well (Table 1). This IL-2-induced proliferation was preserved even in the presence of 1.0 μg/ml of Stx1A, a toxin concentration sufficient to cause almost complete suppression of SLP. Moreover, proliferation in these cultures exceeded proliferation in cultures of BLV-negative PBMC treated with combination of Stx1A and IL-2 (Table 1).

TABLE 1

The effect of Stx1 A and IL-2 on the
proliferation of BLV-positive and BLV-negative PBMC.

| PBMC | Stx1 A[a] | IL-2 0 | 0.1 ng/ml | 1.0 ng/ml |
|---|---|---|---|---|
| BLV-Positive | 0 | 77.3 ± 4.8[b] | 97.3 ± 3.2 | 136 ± 1.5 |
|  | 0.1 µg/ml | 38.3 ± 1.3 | 60.5 ± 1.9 | 123 ± 1.1 |
|  | 1.0 µg/ml | 10.0 ± 0.8 | 22.1 ± 0.2 | 61.5 ± 2.2 |
| BLV-Negative | 0 | 0.7 ± 0.04 | 6.8 ± 0.6 | 42.5 ± 0.3 |
|  | 0.1 µg/ml | 0.5 ± 0.1 | 6.8 ± 0.7 | 34.1 ± 0.5 |
|  | 1.0 µg/ml | 1.0 ± 0.2 | 5.7 ± 0.2 | 25.9 ± 1.1 |

[a]toxin and IL-2 were added at the start of the cell culture
[b]mean CPM × $10^{-3}$ ± SE of four measurements from a typical experiment.

BLV-positive cultures treated with Stx1A also retained the ability to respond to stimulation with PWM. These results indicate that inhibition of SLP by Stx1 involves selective action on a sub-population of PBMC and does not alter the ability of B cells not targeted by the toxin to respond to immunostimulation. Additional support for the premise that Stx1 targets a selected and probably minor subpopulation of B cells comes from the finding that cell death, detected by trypan blue inclusion or cell shrinkage measured by flow cytometry, was not increased in cultures treated with Stx1A. This finding is consistent with the fact that although the majority of B-cells from cows in PL stage contain provirus, very few PBMC from BLV-positive cattle express viral proteins (Baliga & Ferrer 1977; Gupta et al. 1984; Chatterjee et al. 1985; Levy et al. 1987).

The impact of Stx1A on PBMC cultures stimulated with lipopolysaccharide (LPS) was also examined. This gram-negative bacteria cell wall component can significantly influence immune responses, and was shown to stimulate BLV expression in cultures of BLV-positive PBMC (Kidd & Radke 1996). LPS used at concentration of 0.1 μg/ml increased proliferation of BLV-positive PBMC twofold but did not induce normal PBMC cultures to proliferate, indicating that only BLV-positive cultures were susceptible to mitogenic stimulation by low concentrations of LPS. The increased proliferation resulting from LPS application was completely abrogated by treatment with Stx1A, further indicating that cells involved in SLP constitute the cellular targets of Stx1A.

Anti-Stx1A serum prevents inhibition of SLP by Stx1. To determine if a spurious inhibitor was present in the toxin preparations, the ability of anti-Stx1A immune serum to neutralized Stx1 or Stx1A suppression of SLP was tested. Antitoxin neutralized Stx1 or Stx1A activity in a dose-dependent manner (FIG. 2) and did not affect cellular proliferation in cultures without toxin. The antitoxin was effective within a range of titers from 1:1000 to 1:50, but did not have a neutralizing ability outside this range. Within this range the ability of antitoxin to neutralize increasingly greater doses of Stx1A was directly proportional to concentration. For example, antitoxin restored about 80% to >50% of the thymidine incorporation in BLV-positive cultures treated with up to 1.0 μg/ml Stx1A or Stx1, respectively (FIG. 2). A two-way ANOVA indicated statistically significant differences among the effects of various concentrations of toxin and antitoxin as well as a significant interaction of these two factors.

Inhibition of SLP by antiviral antibody or Stx1A is similarly time-dependent. SLP in cultures of BLV-positive PBMC is preceded within 24 hr of culture by de novo synthesis of viral proteins and dissemination of viral particles (Baliga & Ferrer 1977). It is known that anti-BLV serum can block SLP (Trueblood et al. 1998). To assess whether viral proteins accessible to antibody were required to sustain SLP, the ability of antiviral antibody to interfere with SLP over a two-day period was examined. Monoclonal anti-gp51 was able to reduce thymidine incorporation in spontaneously proliferating cultures by 60% (FIG. 3). However, this inhibition required application of anti-gp51 at the beginning of cell culture (FIG. 3). Inhibition of SLP by anti-gp51 was due to a specific interaction with viral proteins, because this antibody did not affect IL-2-induced proliferation of BLV-negative PBMC, and control monoclonal antibody of the same isotype had no effect on SLP. These results are in agreement with the findings that dissemination of BLV proteins is involved in initiation of SLP, but they also suggest that BLV proteins are not required for continuation of an established SLP event.

To determine if toxin also acts on SLP in a time-dependent fashion, Stx1A or Stx1B was administered to cultures of BLV-positive PBMC at various times after the start of cell culture. Similar to treatment with anti-gp51, the ability of Stx1A to inhibit SLP was reduced if cells were precultured in medium for 24 hours before toxin application (FIG. 3). Stx1A applied on day 2 of culture at concentrations of up to 1.0 μg/ml had only minimal impact upon SLP (FIG. 3) and even 5.0 μg/ml Stx1A applied on day 2 of culture reduced thymidine incorporation in spontaneously proliferating cultures by only 30 to 40%. These results suggest that inhibition of SLP by Stx1A is time-dependent, and may be based on the ability of the toxin to interfere with the initiation of spontaneous proliferation. The fact that susceptibility of SLP to inhibition by either Stx1A or anti-gp51 lessens within 24 hours of culture evidences that the cells involved in dissemination of viral proteins and the initiation of SLP constitute targets for Stx1.

In contrast to Stx1A, the relatively minor effect of Stx1B on SLP did not change when Stx1B was applied after a preculture without toxin. This difference suggests that Stx1B and Stx1A have different modes of action, and likely affect different subpopulations of PBMC.

Stx1A reduces expression of BLV core protein. To directly test antiviral activity of Stx1, the expression of BLV p24 core protein in PBMC cultured with or without Stx1A was assayed. Immunoblot analysis of cell lysates of PBMC cultured for 12 hr showed a reduction in the amount of p24 protein in cells treated with 1.0 μg/ml toxin compared to cells in the control cultures without toxin (FIG. 4). The optical density of the immunoreaction in the sample treated with toxin was 442-fold less than the immunoreaction in the sample without toxin, suggesting that toxin suppressed viral protein synthesis.

The results demonstrate the antiviral activity of Stx. The results are consistent with research showing antiviral activity of the RIP family of toxins (reviewed in Stirpe et al. 1992). The results also demonstrate that Stx1 is a potent suppressor of SLP and that this activity is mediated by the A subunit of Stx1. The most likely explanation for this result is that Stx1 has an adverse impact on the cells that express the virus. It is well established that SLP is preceded and accompanied by synthesis of viral proteins (Takashima & Olson 1981; Kerkhofs et al. 1996). The premise that Stx1 has antiviral activity is supported by the fact that maximal SLP sensitivity to Stx1 was exhibited within the first 24 hours of culture. A similar time-dependent loss of sensitivity of SLP to antigp51-mediated inhibition was also found. Both these findings are consistent with the fact that the expression of BLV particles in culture reaches maximum after 12 to 24 hr of cell culture (Zandomeni et al. 1992). Inhibition of SLP by BLV-specific antibody is well established (Thorn et al. 1981; Trueblood et al. 1998), and possibly results from the interference with the release of BLV particles from cultured cells (Driscoll et al. 1977).

The reduced expression of BLV p24 protein in cell cultures treated with Stx1 could be due either to the nonlethal suppression of viral protein synthesis or Stx1-mediated lysis of the cells expressing viral proteins. The assay did not allow distinction between these possibilities because the determination of the p24 protein level was limited to the protein present within cells harvested from the cell cultures at a given time.

The suppression of SLP by Stx1 did not diminish the ability of B-cells in BLV-positive PBMC cultures to respond to immunostimulation by IL-2 or PWM. This implies that Stx1 suppresses SLP via a selective mechanism and is consistent with the fact that very few B cells in BLV-infected cattle express viral proteins or viral particles (Gupta et al. 1984). Moreover, Stx1 had little effect on PWM-induced normal bovine B-cell proliferation and no adverse effect on ConA-induced bovine T-cell proliferation. These findings support the premise of a selective antiviral activity of Stx1. Especially relevant is the fact that Stx1 was a potent SLP inhibitor at low concentrations, which had only marginal impact on normal PBMC.

Similar to ricin, the archetype of the A:B RIPs, Stx1 holotoxin is composed of an enzymatically active A-chain and a cell-receptor binding B-chain pentamer. The A subunit alone was able to abrogate SLP and, compared to holotoxin, was similarly efficacious. Thus, sensitivity of target cells in BLV-positive culture to Stx1 occurs via a mechanism that does not require the B subunit. This is in a sharp contrast to the receptor-based mechanism by which Stx1 gains entry to Vero cells and other cellular targets described (Jackson 1990; Bast et al. 1997). However, antiviral activity of the plant RIP proteins also does not require a B subunit. Class 1 RIPs composed solely of an enzymatic A chain are potent antiviral agents; examples include inhibition of HIV replication by pokeweed antiviral protein (Olson et al. 1991), bryodin (Wachinger et al. 1993), and trichosanthin (Byers et al. 1994). Similar anti-HIV activity is exhibited by an isolated A chain of ricin (Neukirch et al. 1981). Typically, inhibition of HIV-1 replication by plant RIP proteins occurs at the concentrations nontoxic to uninfected cells (Olson et al. 1991; Lee-Huang et al. 1995).

Inhibition of protein synthesis may not be the only mechanism of antiviral activity. Plant RIP proteins were shown to inhibit HIV-1 integrase via topological activity on long terminal repeats of viral DNA (Lee-Huang et al. 1995), and these proteins show structural similarities to retroviral reverse transcriptases (Ready et al. 1988). Inhibition of HIV infection by plant RIPs involves regions of these proteins which are not required for ribosome inactivation, suggesting that the anti-HIV activity of ribosome-inactivating proteins may not be the result of N-glycosidase activity alone (Lee-Huang et al. 1994).

Interestingly, some antiviral activity of RIPs has been associated with the B subunit. For instance, ricin can agglutinate hog cholera virus (a small RNA virus) due to a galactose-binding ability of B subunit (Neukirch et al. 1981). Ricin was also able to agglutinate cells of a variety of leukemic cell lines, including NIH3T3 cells infected with Moloney leukemia virus (Koga et al. 1979). These results agree with our finding that, although less efficaciously than Stx1A, Stx1B subunit was able to inhibit SLP to some degree. However, Stx1B-mediated inhibition of SLP was not time-sensitive, and was inferior to Stx1A at equivalent molar concentrations, further indicating that the mechanism of Stx1B action is different than that of Stx1A.

Example 2

Suppression of Bovine Leukemia Virus-Related Cell Proliferation by Administering to Cows a Probiotic E. coli Expressing Stx1A In this example, the suppression of BLV-related cell proliferation by administering a representative probiotic E. coli expressing Stx1A is described.

Materials and Methods. The techniques of amplification of genetic sequences with the polymerase chain reaction, cutting and splicing DNA into plasmids, transformation of bacteria with plasmids, and assays for antibody binding are all well known biotechnology methods and detailed descriptions of these methods can be found in a number of texts, for example Sambrook et al. (1989).

Commonly used procaryotic control sequences, which are defined herein to include transcription initiation, optionally operator, and ribosome binding site sequences, can include commonly used promoters such as the beta-lactamase (penicillinase) and lactose (lac) promoter systems (Chang et al. 1977), the tryptophan (trp) promoter system (Goeddel et al. 1980), and the lambda derived $P_L$ promoter and N-gene ribosome binding site (Shimatake et al. 1981). However, any available promoter system compatible with procaryotes can be used.

The successful expression attained by the invention depends upon correct utilization of the suitable control sequences to regulate expression of the desired toxin fragment. Therefore, control sequences compatible with and suitable for the host are positioned operably with respect to the coding sequence, using a properly placed "start" codon at the 5' end of the desired sequence. Any "native" control sequences are eliminated. The vectors of the invention place the coding sequence for Stx1A, immediately preceded by an ATG start codon directly downstream from control systems chosen to be compatible with the particular host.

It is also important, in obtaining good production of Stx1A, to regulate the "time" of production so as to minimize any lethal effect on the host cell. Most typically, even for procaryotes, this is done by delaying expression of the toxin sequences until substantial growth has occurred. Accordingly, it is desirable to utilize control sequences that are subject to environmental conditions. By maintaining conditions that repress expression during growth phase, and then converting to conditions which permit expression at the desired time, the negative aspects of any potentially lethal effect can be minimized. Inducible expression systems that have been used successfully to express ricin toxin, another class 2 RIP (see U.S. Pat. No. 6,084,073), are described below.

The trp promoter is a regulatable promoter where expression of the operably linked sequence can be controlled by the level of tryptophan in the medium. By maintaining high tryptophan levels during growth, expression is repressed. Depletion or competitive inhibition of tryptophan turns on the promoter and permits expression.

The $P_L$ promoter derived from lambda phage is regulated by a protein that can be temperature sensitive. Mutant forms of the wild type repressor, e.g., $CI_{857}$, having this characteristic are known. When used in a host that is able to synthesize this mutant form of repressor, the $P_L$ promoter will be switched on when the temperature is raised because the higher temperature inactivates the mutant CI repressor. Thus, the host cells can be grown at low temperature without, or with, low production of the foreign protein. The temperature is then raised when growth has been attained and Stx1A production is desired.

When the phoA control sequences are employed, expression can be delayed by maintaining the cells in the presence of phosphate ion and then depleting the phosphate levels when expression is desired.

A plasmid that has temperature sensitive copy number control may also be applied. If the cells are grown at low temperatures, coding sequences contained in the plasmid are replicated at low levels; at higher temperatures, the number of such copies is increased. The amount of protein produced is thus indirectly managed by regulating the number of available copies or its coding sequence.

Vector construction employs known ligation and restriction technique. A method for achieving intracellular expression of Shiga-toxin polypeptides in E. coli has been previously described (Zollman, et al. 1994; Austin & Hovde 1995). Similar expression vectors and techniques, as well as others described above, can be used to direct expression of Shiga-toxin polypeptides in a probiotic E. coli. Any generic nonpathogenic bovine strain could be used, or a recA minus lab strain, for example strains E. Coli 271 ATCC 202020, E. coli 786 ATCC 202018, and E. coli ATCC 202019 described in U.S. Pat. No. 5,965,128.

The expression vectors containing Stx1A coding sequences are transformed into the appropriate strains of E. coli and the cells grown under standard culture conditions. Sonicated extracts are analyzed for protein production using Western blot as previously described (Hovde et al. 1988).

The probiotic E. coli expressing Stx1A can be orally administered to (1) BLV-infected cows at the asymptomatic stage of infection, (2) BLV-infected cows at the PL stage of infection, (3) BLV-infected cows at the malignant lymphosarcoma stage of infection, and (4) uninfected cows.

In order to determine the effective dose of Stx1A, the titers of anti-BLV antibodies in treated cows are measured at regular intervals after the start of the treatment protocol. In addition, PBMC are isolated from treated cows and proliferation assays and BLV expression assays are performed as described in Example 1.

Example 3

Suppression of Bovine Leukemia Virus-Related Cell Proliferation by Administering to Cows a Transgenic Plants Expressing Stx1A In this example, the suppression of BLV-related cell proliferation by administering a representative transgenic plant expressing Stx1A is described.

Materials and Methods. The techniques of amplification of genetic sequences with the polymerase chain reaction, cutting and splicing DNA into plasmids, transformation of bacteria with plasmids, and assays for antibody binding are all well known biotechnology methods and detailed descriptions of these methods can be found in a number of texts, for example Sambrook et al. (1989).

The coding sequence for Stx1A is inserted into the 30B expression vector (Shivprasad et al. 1999). This tobacco mosaic virus-based expression vector contains a heterologous coat protein subgenomic mRNA promoter and a heterologous 3' nontranslated region. In previous experiments, expression regulated by this vector resulted in accumulation of up to 10% of soluble protein in leaves (Shivprasad et al. 1999). The techniques of amplification of genetic sequences with the polymerase chain reaction (PCR), cutting and splicing DNA into plasmids, transformation of bacteria with plasmids, and assays for antibody binding are all well known biotechnology methods and detailed descriptions of these methods can be found in a number of texts including Sambrook et al. (1989).

Tobacco plants and Chenopodium quinoa plants are infected with the Stx1A expression construct as previously described (Lewandowski & Dawson 1988). To prepare DNA for the transcription reaction, 25 µg of the plasmid are linearized with the appropriate restriction enzyme and purified by phenol/chloroform extraction and ethanol precipitation to remove all RNAases. The DNA is then resuspended in water to a concentration of 1.25 to 2.5 µg in a volume of 12 µl. The transcription reaction cocktail contains 2.5 µl of 10×Ty RNA polymerase buffer (New England Biolabs), 2.5 µl 100 mM DTT (Gibb BRL), 0.5 µl Rnasin (Promega), 1.25 µl 10×NTPs (ATP, CTP, UTP: 20 mM, GTP: 2 mM; Amersham-Pharmacia), 4.0 µl 25 mM $MgCl_2$ (Gibb BRL), 1.25 µl 5 mM cap analogue (Diguanosine Triphosphate; Amersham-Pharmacia), and 1.25 to 2.5 µg of linearized plasmid DNA. The reaction is mixed and incubated at 37° C. for 2 minutes, after which 1 µl of T7 RNA polymerase (New England Biolabs) is added. The reaction is further incubated at 37° C. for 15 minutes, then 2 µl of 12.5 mM GTP is added. This is followed by incubation at 37° C. for an additional 75 minutes. For plant inoculation, plants are kept in the dark overnight prior to dusting. 25 µl of DEPC-treated water and 50 µl of FES buffer are gently mixed. Prior to inoculation, the leaves are dusted with carborundum. 10–15 µl of the transcription reaction is rubbed on to each leaf of the plant.

The expression of Stx1A in transgenic plants is demonstrated by Western analysis or Ouchterlonay. Fresh plant tissue is weighed and frozen at −80° C. or liquid nitrogen. The tissue is then ground with a mortar and pestle until it is powderized. To this powder, PBST (5 mM phosphate/140 mM NaCl/0.05% Tween 20, pH 7.2) is added to a final concentration of 0.5M PBST per gram and thoroughly ground. About 1.2 ml of the mixture is then transferred to a microfuge tube and centrifuged at 14,000 rpm for 10 minutes at 4° C. For Ouchterlonay, 20 µl is added per well. For Western analysis, 200 µl is mixed with 50 µl SDS loading buffer and 20–25 µl is added per well. Subsequent Western analyses are performed according to standard protocols.

The transgenic plants expressing Stx1A can be orally administered to (1) BLV-infected cows at the asymptomatic stage of infection, (2) BLV-infected cows at the PL stage of infection, (3) BLV-infected cows at the malignant lymphosarcoma stage of infection, and (4) uninfected cows.

In order to determine the effective dose of transgenic plants expressing Stx1A, the titers of anti-BLV antibodies in treated cows are measured at regular intervals after the start of the treatment protocol. In addition, PBMC are isolated from treated cows and proliferation assays and BLV expression assays are performed as described in Example 1.

REFERENCES

Acheson, D. W. K., R. Moore, S. DeBreucker, L. Lincicome, M. Jacewicz, E. Skutelsky, and G. T. Keusch, "Translocation of Shiga toxin across polarized intestinal cells in tissue culture" Infect. Immun. 64:3294–3300 (1996).

Agresti, A., Ponti, W., Rocchi, M., Meneveri, R., Marozzi, A., Cavalleri, D., Peri, E., Poli, G. and E. Ginelli, "Use of polymerase chain reaction to diagnose bovine leukemia virus infection in calves at birth" *Amer. J. Vet. Res.* 54:373–378 (1993).

An et al., *Plant Physiology* 81:301–305 (1986).

Austin, P. R., and C. J. Hovde, "Purification of Recombinant Shiga-like Toxin Type I B Subunit" *Protein Expression and Purification* 6:771–779 (1995).

Baliga, V., and J. F. Ferrer, "Expression of the bovine leukemia virus and its internal antigen in blood lymphocytes" *Proc Soc Exp Biol Med.* 156(2):388–91 (1977).

Bast, D. J., J. Sandhu, N. Hozumi, B. Barber, and J. Brunton, "Murine antibody responses to the verotoxin 1 B subunit: demonstration of major histocompatibility complex dependence and an immunodominant epitope involving phenylalanine 30" *Infect. Immun.* 65:2978–2982 (1997).

Benini, F., Canevari, S., Gadina, M., Adobati, E., Ferreri, A. J., Di Celle, E. F., Comolli, R., and Colnaghi, M. I., "Preclinical evaluation of the ribosome-inactivating proteins PAP-1, PAP, -S, and RTA in mice" *Int. J. Immunopharmacol.* 17:829–839 (1995).

Birch, *Ann Rev Plant Phys Plant Mol Biol* 48:297 (1997).

Bruck, C., N. Rensonnet, D. Portetelle, Y. Cleuter, M. Mammerickx, A. Burny, R. Mamoun, B. Guillemain, M. J. van der Maaten, and J. Ghysdael, "Biologically active epitopes of bovine leukemia virus glycoprotein gp51: their dependence on protein glycosylation and genetic variability" *Virology*, 136(1):20–31 (1994).

Byers, V. S., A. S. Levin, A. Malvino, L. Waites, R. A. Robins, and R. W. Baldwin, "A phase II study of effect of addition of trichosanthin to zidovudine in patients with HIV disease and failing antiretroviral agents" *AIDS Res Hum Retroviruses*, 10(4):413–20 (1994).

Chang, A. C. et al., *Nature* 198:1056 (1977).

Chang, A. C., Nunberg, J. H., Kaufman, R. J., Erlich, H. A., Schimke, R. T. and S. N. Cohen, "Phenotypic expression in *E. coli* of a DNA sequence coding for mouse dihydrofolate reductase" *Nature* 375:617–24 (1978).

Chatterjee, R., P. Gupta, S. V. Kashmiri, and J. F. Fewer, "Phytohemagglutinin activation of the transcription of the bovine leukemia virus genome requires de novo protein synthesis" *J. Virol.* 54(3):860–3 (1985).

Cockerell, G. L. et al., *Leuk. Res.* 12:465–469 (1988).

Da, et al., "Milk and fat yields decline in bovine leukemia virus-infected Holstein cattle with persistent lymphocytosis," *Proc. Natl. Acad. Sci.* 90:6538 (1993).

Driscoll, D. M., M. Onuma, and C. Olson, "Inhibition of bovine leukemia virus release by antiviral antibodies" *Arch Virol.*, 55(1–2):139–44 (1977).

Dropulic, B. et al., *J. Virol.* 66:1432–1441 (1992).

Elmer et al., *JAMA* 275: 870–876 (1996).

Endo, Y., K. Mitsui, M. Motizuki, and K. Tsurugi, "The mechanism of action of ricin and related toxic lectins on eukaryotic ribosomes. The site and the characteristics of the modification in 28 S ribosomal RNA caused by the toxins" *J Biol. Chem.*, 262:5908–5912 (1987).

Endo, Y., K. Tsurugi, T. Yutsudo, Y. Takeda, T. Ogasawara, and K. Igarashi, "Site of action of a Vero toxin (VT2) from *Escherichia coli* 0157:117 and of Shiga toxin on eukaryotic ribosomes. RNA {IN}-glycosidase activity of the toxins" *Europ. J. Biochem.*, 171:45–50 (1988).

Esteban, E. N., R. M. Thorn, and J. F. Ferrer, "Characterization of the blood lymphocyte population in cattle infected with the bovine leukemia virus" *Cancer Res.*, 45(7):3225–30 (1985).

Ferens, W. A., W. C. Davis, M. J. Hamilton, Y. H. Park, C. F. Deobald, L. Fox, and G. Bohach, "Activation of bovine lymphocyte subpopulations by staphylococcal enterotoxin C." *Infect Immun.* 66(2):573–80 (1998).

Ferrer, J. F., R. R. Marshak, D. A. A M, and S. J. Kenyon, "Relationship between lymphosarcoma and persistent lymphocytosis in cattle: a review" *J Am Vet Med Assoc.*, 175(7):705–8 (1979).

Ferrer, J. F., "Bovine lymphosarcoma" *Adv Vet Sci Comp Med.*, 24:1–68 (1980).

Forester et al., *Exp. Agric.* 33:15–33 (1997).

Fuller, R., "Probiotics in Man and Animals—A Review" *J of Applied Bacteriol.*, 1989. 66, pp.365–378.

Goeddel, D. V., Heyneker, H. L., Hozumi, T., Arentzen, R., Itakura, K., Yansura, D. G., Ross, M. J., Miozzari, G., Cream R. and P. H. Seeburg, "Direct expression in *Escherichia coli* of a DNA sequence coding for human growth hormone" *Nature* 281:544–48 (1979).

Goeddel et al., *Nucl. Acids Res.* 8:4057 (1980).

Gupta, P., S. V. Kashmiri, and J. F. Ferrer, "Transcriptional control of the bovine leukemia virus genome: role and characterization of a nonimmunoglobulin plasma protein from bovine leukemia virus-infected cattle" *J. Virol.*, 50(1):267–70 (1984).

Hanahan, D., Jessee, J. and F. R. Bloom, "Plasmid transformation of *Escherichia coli* and other bacteria" *Meth. Enxymol.*, 204:63–113. (1991).

Hino, M., T. Sekizawa, and H. Openshaw, "Ricin injection eliminates latent herpes simplex virus in the mouse [letter]" *J Infect Dis.* 157(6):1270–1 (1988).

Hoeckema et al., *Nature* 303:179–181 (1983)

Hooykaas, P. J., "Transformation of plant cells via Agrobacterium" *Plant Mol. Biol.* 13:327–36 (1989).

Hovde, C. J., S. B. Calderwood, J. J. Mekalanos, and R. J. Collier, "Evidence that glutamic acid 167 is an active-site residue of Shiga-like toxin" *J. Proc. Nat. Acad. Sci. USA*, 85:2568–2572 (1988).

Howie, M., "Bovine Leukosis Virus is prevalent, costly to U.S. Dairy Operations," Feedstuffs 69:11 (1997).

Itakura, K., Hirose, T., Crea, R., Riggs, A. D., Heyneker, H. L., Bolivar, F. and H. W. Boyer, "Expression in *Escherichia coli* of a chemically synthesized gene for the hormone somatostatin" *Science* 198:1056 (1977).

Jackson, M., "Structure-function analyses of Shiga toxin and the Shiga-like toxins" *Microbial Pathogenesis*, 8:235–242 (1990).

Jensen, W. A., S. E. Sheehy, M. H. Fox, W. C. Davis, and G. L. Cockerell, "In vitro expression of bovine leukemia virus in isolated B-lymphocytes of cattle and sheep" *Vet Immunol Immunopathol.*, 26(4):333–4.2 (1990).

Kerkhofs, P., E. Adam, L. Droogmans, D. Portetelle, M. Mammerickx, A. Burny, R. Kettmann, and L. Willems, "Cellular pathways involved in the ex vivo expression of bovine leukemia virus" *J. Virol.*, 70(4):2170–7 (1996).

Kettmann, R., D. Portetelle, M. Mammerickx, Y. Cleuter, D. Dekegel, M. Galoux, J. Ghysdael, A. Burny, and H.

Chantrenne, "Bovine leukemia virus: an exogenous RNA oncogenic virus" *Proc. Natl. Acad. Sci. USA,* 73(4):1014–8 (1976).

Kidd, L. C., and K. Radke, "Lymphocyte activators elicit bovine leukemia virus expression differently as symptomatic infection progresses" *Virology,* 217(1):167–77 (1996).

Koga, M., M. Ohtsu, and G. Funatsu, "Cytotoxic, cell agglutinating, and syncytium forming effect of purified lectins from *Ricinus communis* on cultured cells" *Gann.,* 70(5):585–91 (1979).

Lee-Huang, S., P. L. Huang, A. S. Bourinbaiar, H. C. Chen, and H. F. Kung, "Inhibition of the integrase of human immunodeficiency virus (HIV) type 1 by anti-HIV plant proteins MAP30 and GAP31" *Proc. Natl. Acad. Sci. USA,* 92(19):8818–22 (1995).

Lee-Huang, S., H. F. Kung, P. L. Huang, A. S.~Bourinbaiar, J. L. Morell, J. H. Brown, W. P. Tsai, A. Y. Chen, H. I. Huang, and et al., "Human immunodeficiency virus type 1 (HIV-1) inhibition, DNA binding, RNA binding, and ribosome inactivation activities in the N-terminal segments of the plant anti-HIV protein GAP31" *Proc. Natl. Acad. Sci. USA,* 91(25):12208–12 (1994).

Levy, D., R. Kettmann, P. Marchand, S. Djilali, and A. L. Parodi, "Selective tropism of bovine leukemia virus (BLV) for surface immunoglobulin-bearing ovine B lymphocytes" *Leukemia,* 1(5):463–5 (1987).

Lewandoski, D. J., and W. O. Dawson, "Deletion of internal sequences results in tobacco mosaic virus defective RNAs that accumulate to high levels without interfering with replication of the helper virus" *Virology* 251:427–37 (1998).

Mammerickx, M. et al., *Leuk Res.* 11:353–358 (1987).

Menge, C., L. H. Wieler, T. Schlapp, and G. Baller, "Shiga toxin 1 from *Escherichia coli* blocks activation and proliferation of bovine lymphocyte subpopulations in vitro" *Infect. Immun.,* 67(5):2209–17 (1999).

Morgan et al., *AIDS Res. Hum. Retrovir.* 10: 1507–1515 (1994).

Miller, et al., *Annales de Recherches Veterinaires* 9:871 (1978).

Miller, L. D. et al., *Amer. J. Vet. Res.* 46:808–814 (1985).

Mirsky, M. L., C. A. Olmstead, Y. Da, and H. A. Lewin, "The prevalence of proviral bovine leukemia virus in peripheral blood mononuclear cells at two subclinical stages of infection" *J. Virol.* 70(4):2178–83 (1996).

Neukirch, M., V. Moennig, and B. Liess, "A simple procedure for the concentration and purification of hog cholera virus (HCV) using the lectin of *Ricinus communis*" *Arch Virol.,* 69(3–4):287–90 (1981).

Olson, M. C., S. Ramakrishnan, and R. Anand, "Ribosomal inhibitory proteins from plants inhibit HIV-1 replication in acutely infected peripheral blood mononuclear cells" *AIDS Res Hum Retroviruses,* 7(12):1025–30 (1991).

Pirro, F., L. H. Wieler, K. Failing, R. Bauerfeind, and G. Baljer, "Neutralizing antibodies against Shiga-like toxins from *Escherichia coli* in colostra and sera of cattle" *Vet Microbiol.,* 43(2–3):131–41 (1995).

Portetelle, D., C. Bruck, M. Mammerickx, and A. Burny, "In animals infected by bovine leukemia virus (BLV) antibodies to envelope glycoprotein gp51 are directed against the carbohydrate moiety" *Virology,* 105(1):223–33 (1980).

Ready, M. P., B. J. Katzin, and J. D. Robertus, "Ribosome-inhibiting proteins, retroviral reverse transcriptases, and RNase H share common structural elements" *Proteins,* 3(1):53–9 (1988).

Sambrook et al., "Molecular Cloning-A Laboratory Manual" Cold Spring Harbor Laboratory, Cold Spring Harbor, N.Y. 1989.

Shivprasad, S. G., and G. P. Porgue et al., "Heterologous sequences greatly affect foreign gene expression in tobacco mosaic virus-based vectors" *Virology* 255:312–23 (1999).

Schultz, S., Lopez, M. J., Kuhn, M. and D. L. Garbers, "Disruption of the guanylyl cyclase-C gene leads to a paradoxical phenotype of viable but heat-stable enterotoxin-resistant mice" *J. Clin. Invest.,* 100:1590–95 (1997).

Siebenlist, U., Simpson, R. B. and W. Gilbert, "*E. coli* RNA polymerase interacts homologously with two different promoters" *Cell* 20:269–91 (1980).

Shimatake, et al., *Nature* 292:128 (1981).

Sparapani, M., Buonamici, L, Ciani, E., Battelli, M. G., Ceccarelli, G., Stirpe, F., and Contestabile, A., "Toxicity or ricin and volkensin, two ribosome-inactivating proteins, to microglia, astrocyte, and neuron cultures" *Glia* 20:203–209 (1997).

Stirpe, F., L. Barbieri, M. G. Battelli, M. Soria, and D. A. Lappi, "Ribosome-inactivating proteins from plants: Present status and future prospects" *Bio-Technology,* 10:405–412 (1992).

Takashima, I., and C. Olson, "Relation of Bovine leukosis virus production on cell growth cycle" *Arch Virol.,* 69(2):141–8 (1981).

Theilen, G. H., "Methods of protecting cattle and sheep against bovine leukemia virus and vaccines for use therein," U.S. Pat. No. 4,323,555 (1982).

Thorn, R. M., P. Gupta, S. J. Kenyon, and J. F. Ferrer, "Evidence that the spontaneous blastogenesis of lymphocytes from bovine leukemia virus-infected cattle is viral antigen specific," *Infect Immun.,* 34(1):84–9 (1981).

Trueblood, E. S., W. C. Brown. G. H. Pahner, W. C. Davis, D. M. Stone, and T. F. McElwain, "B-lymphocyte proliferation during bovine leukemia virus-induced persistent lymphocytosis is enhanced by T-lymphocyte-derived interleukin-2." *J Virol.,* 72(4):3169–77 (1998).

Wachinger, M., R. Samtleben, C. Gerhauser, H. Wagner, and V. Erfle, "Bryodin, a single-chain ribosome-inactivating protein, selectively inhibits the growth of HIV-1-infected cells and reduces HIV-1 production" *Res Exp Med.,* 193(1):1–12 (1993).

Watanabe, K., T. Kawasaki, N. Sako, and G. Funatsu, "Actions of pokeweed antiviral protein on virus-infected protoplasts" *Biosci. Biotechnol. Biochem.,* 61:994–997 (1997).

Weber, A. F. et al., Amer. J. Vet. Res. 44:1912–1915 (1983).

Wittman, et al., *Arch. Exp. Veterinaermed* 23:709 (1989).

Yoshida, T., M. Fukada, N. Koide, H. Ikeda, T. Sugiyama, Y. Kato, N. Ishikawa, and T. Yokochi, "Primary cultures of human endothelial cells are susceptible to low doses of Shiga toxins and undergo apoptosis" *J. Infect. Dis.* 180:2048–2052 (1999).

Zandomeni, R. O., M. Carrera-Zandomeni, E. Esteban, W. Donawick, and J. F. Ferrer, "Induction and inhibition of bovine leukaemia virus expression in naturally infected cells" *J Gen Virol.,* 73(Pt 8):1915–24 (1992).

Zollman, T. M., P. R. Austin, P. E. Jablonski, and C. J. Hovde, "Purification of recombinant Shiga-like toxin type I A {-}1 fragment from *Escherichia coli*" *Protein Expression and Purification,* 5:291–295 (1994).

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method for suppressing bovine leukemia virus-related cell proliferation in an animal subject, comprising administering an amount of a composition comprising a Stx1A polypeptide to the animal effective to suppress bovine leukemia virus-related cell proliferation.

2. The method of claim 1, wherein the animal subject is a ruminant.

3. A method for treating a bovine leukemia virus-related disorder in an animal subject, comprising administering to the animal subject an amount of a composition comprising a Stx1A polypeptide effective to suppress bovine leukemia virus-related cell proliferation in the animal subject.

4. The method of claim 3, wherein the bovine leukemia virus-related disorder comprises persistent lymphocytosis.

5. The method of claim 3, wherein the bovine leukemia virus-related disorder comprises malignant lymphoma.

6. The method of claim 3, wherein the bovine leukemia virus-related disorder comprises the progression of viral infection.

7. The method of claim 3, wherein the animal subject is a ruminant.

8. A method for treating a cell, comprising administering to the cell an amount of a Stx1A polypeptide effective to suppress bovine leukemia virus-related cell proliferation.

9. The method of claim 8, wherein the cell is infected with bovine leukemia virus.

* * * * *

UNITED STATES PATENT AND TRADEMARK OFFICE
CERTIFICATE OF CORRECTION

PATENT NO. : 6,541,013 B1
DATED : April 1, 2003
INVENTOR(S) : C.H. Bohach

It is certified that error appears in the above-identified patent and that said Letters Patent is hereby corrected as shown below:

<u>Title page,</u>
Item [56], References Cited, OTHER PUBLICATIONS, "Trueblodd, E.S., et al.," reference, "Trueblodd," should read -- Trueblood, --; and "Zollman, T.M., et al.," reference, "—Like" should read -- Like --

Signed and Sealed this

Fifteenth Day of July, 2003

JAMES E. ROGAN
*Director of the United States Patent and Trademark Office*